(12) United States Patent
Tomidokoro et al.

(10) Patent No.: US 8,408,704 B2
(45) Date of Patent: Apr. 2, 2013

(54) FUNDUS OCULI OBSERVATION DEVICE, OPHTHALMOLOGIC IMAGE PROCESSING DEVICE, AND PROGRAM

(75) Inventors: Atsuo Tomidokoro, Tokyo (JP); Shinsuke Konno, Tokyo (JP); Makoto Araie, Tokyo (JP); Hiroyuki Aoki, Tokyo (JP); Takashi Fujimura, Tokyo (JP); Tsutomu Kikawa, Tokyo (JP)

(73) Assignees: The University of Tokyo, Tokyo (JP); Kabushiki Kaisha Topcon, Tokyo (JP)

( * ) Notice: Subject to any disclaimer, the term of this patent is extended or adjusted under 35 U.S.C. 154(b) by 353 days.

(21) Appl. No.: 12/733,485

(22) PCT Filed: Sep. 9, 2008

(86) PCT No.: PCT/JP2008/002480
§ 371 (c)(1),
(2), (4) Date: Mar. 4, 2010

(87) PCT Pub. No.: WO2009/034704
PCT Pub. Date: Mar. 19, 2009

(65) Prior Publication Data
US 2010/0194757 A1    Aug. 5, 2010

(30) Foreign Application Priority Data
Sep. 10, 2007   (JP) .................. 2007-234695

(51) Int. Cl.
*A61B 3/14*   (2006.01)
(52) U.S. Cl. .................................. 351/206; 351/205
(58) Field of Classification Search .............. 351/205, 351/206, 208, 214, 221, 246; 356/479, 497
See application file for complete search history.

(56) References Cited

U.S. PATENT DOCUMENTS

| | | |
|---|---|---|
| 2007/0159596 A1 | 7/2007 | Fukuma et al. |
| 2007/0159597 A1 | 7/2007 | Fukuma et al. |
| 2007/0285619 A1 | 12/2007 | Aoki et al. |

FOREIGN PATENT DOCUMENTS

| | | |
|---|---|---|
| EP | 1 775 545 A2 | 4/2007 |
| JP | 11-325849 A | 11/1999 |
| JP | 2002-139421 A | 5/2002 |
| JP | 2003-000543 A | 1/2003 |
| JP | 2007-024677 | 2/2007 |
| JP | 2007-130403 | 5/2007 |
| JP | 2007-185243 | 7/2007 |
| JP | 2007-185244 | 7/2007 |
| JP | 2007-325831 | 12/2007 |
| JP | 2008-073099 | 4/2008 |
| WO | WO-2006/022045 A1 | 3/2006 |

OTHER PUBLICATIONS

International Search Report mailed Oct. 7, 2008 issued in International Application No. PCT/JP2008/002480.

*Primary Examiner* — Scott J Sugarman
*Assistant Examiner* — Mahidere Sahle
(74) *Attorney, Agent, or Firm* — Edwards Wildman Palmer LLP

(57) ABSTRACT

A fundus oculi observation device capable of defining which part in the result of analysis of the layer thickness of a fundus oculi is a part obtained by analyzing a vascular region is provided. A fundus oculi observation device 1 forms a plurality of tomographic images G1-Gm of a fundus oculi Ef. A layer thickness distribution calculator 231 calculates layer thickness distribution of the fundus oculi Ef in a cross section of a tomographic image G based on the tomographic images G1-Gm. A vascular region specifying part 234 specifies a vascular region in the tomographic image G. A controller 210 controls a display 240A to display layer thickness distribution information representing the layer thickness distribution and to also display vascular position information representing the position of the vascular region on the layer thickness distribution information.

14 Claims, 15 Drawing Sheets

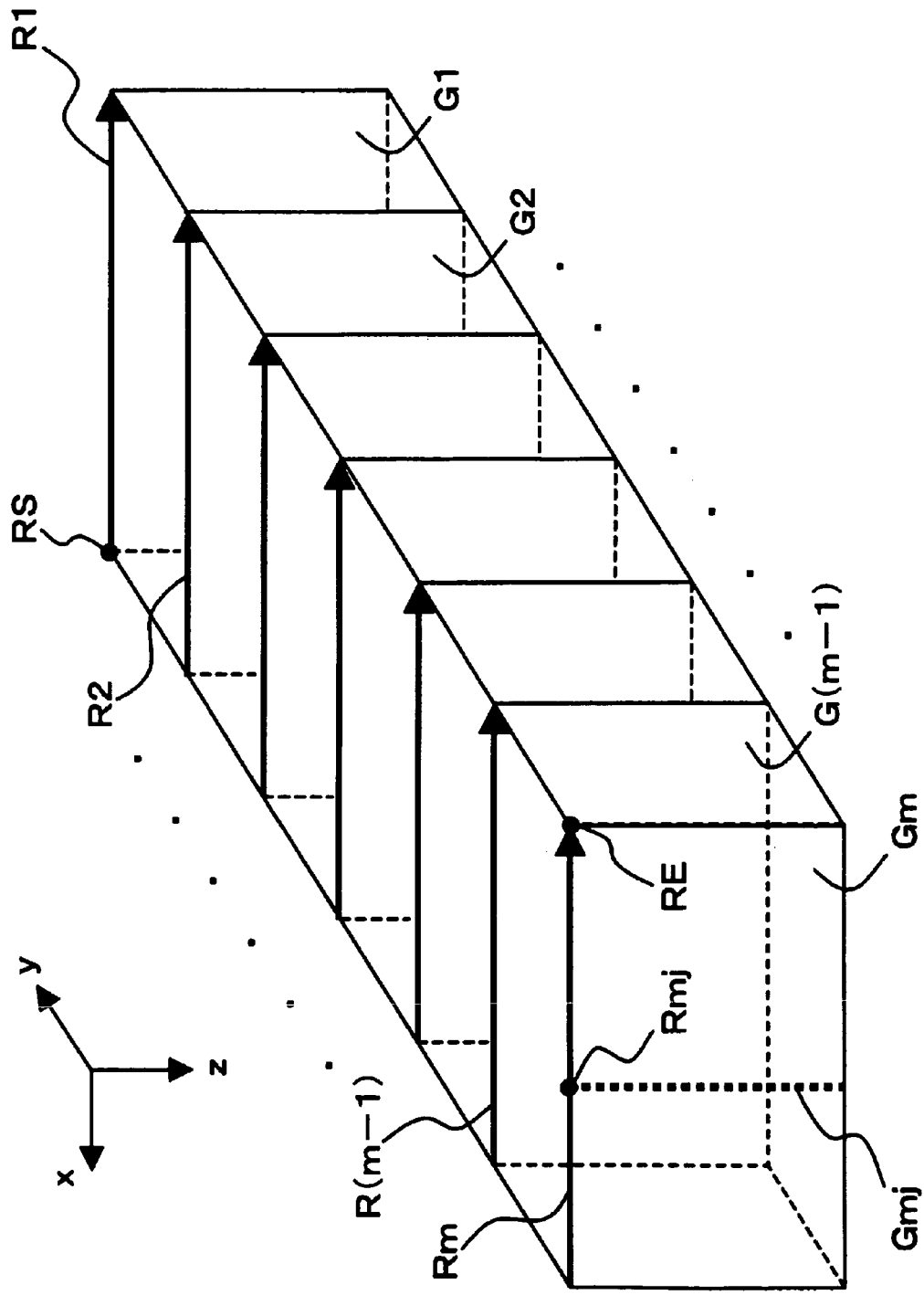

FUNDUS OCULI OBSERVATION DEVICE, OPHTHALMOLOGIC IMAGE PROCESSING DEVICE, AND PROGRAM

TECHNICAL FIELD

The present invention relates to a fundus oculi observation device that radiates a low-coherence light to the fundus oculi and detects an interference light based on the reflected light to form an image of the fundus oculi, and also relates to an opthalmologic image processing device that processes an image of the fundus oculi, and a program for causing a computer to execute processing on an image of the fundus oculi.

BACKGROUND ART

In recent years, such an optical image measurement technique has received attention that forms an image representing the surface morphology or internal morphology of a measured object by using a light beam from a laser light source or the like. Unlike an X-ray CT device, this optical image measurement technique does not have invasiveness to a human body, and therefore, is expected to be applied particularly in the medical field.

Patent Document 1 discloses an optical image measurement device having such a configuration that: a measuring arm scans an object by using a rotary deflection mirror (a Galvano mirror); a reference mirror is disposed to a reference arm; at the outlet thereof, such an interferometer is used that the intensity of a light appearing due to interference of light fluxes from the measuring arm and the reference arm is analyzed by a spectrometer; and the reference arm is provided with a device that gradually changes the light flux phase of the reference light in non-continuous values.

The optical image measurement device disclosed in Patent Document 1 uses a method of the so-called "Fourier Domain OCT (Optical Coherence Tomography)." That is to say, the morphology in the depth direction (the z-direction) of a measured object is imaged by radiating a low-coherence light beam to the measured object, acquiring the spectrum intensity distribution of the reflected light, and subjecting the acquired distribution to Fourier transform.

Furthermore, the optical image measurement device described in Patent Document 1 is provided with a Galvano mirror that scans with a light beam (a signal light) so as to be capable of forming an image of a desired measurement target region of a measured object. Because this optical image measurement device scans with the light beam only in one direction (the x-direction) orthogonal to the z-direction, a formed image is a two-dimensional tomographic image in the depth direction (the z-direction) along a scan direction of the light beam (the x-direction).

Patent Document 2 discloses a technique of scanning with a signal light in the horizontal direction and the vertical direction to thereby form a plurality of two-dimensional tomographic images in the horizontal direction and, based on the plurality of tomographic images, acquiring and imaging three-dimensional tomographic information of a measurement range. As a method for three-dimensional imaging, it is possible to employ, for example, a method of arranging and displaying a plurality of tomographic images in the vertical direction (referred to as stack data or the like), and a method of forming a three-dimensional image by subjecting a plurality of tomographic images to a rendering process.

Patent Document 3 discloses a configuration in which the optical image measurement device as described above is applied in the opthalmologic field. In the opthalmologic field, the optical image measurement device is specifically used as a fundus oculi observation device for observing the fundus oculi. In the fundus oculi, layers such as the retina and the choroidea exist. Moreover, in the retina, the internal limiting membrane, the nerve fiber layer, the ganglion cell layer, the inner plexiform layer, the inner nuclear layer, the outer plexiform layer, the outer nuclear layer, the external limiting membrane, the photoreceptor cell layer and the retinal pigment epithelium layer exist in order from the fundus oculi surface side in the depth direction. The fundus oculi observation device is used for acquiring tomographic images showing the morphologies of these layers. Moreover, it is possible to analyze the thickness of the layer based on the tomographic image. The result of the analysis of the layer thickness is displayed in a graph along the cross-sectional position, for example.

Patent Document 4 discloses an optical image measurement device that executes a measurement while changing the wavelength of a light radiated to a measured object. This optical image measurement device is called the Swept Source type or the like.

[Patent Document 1] Japanese Unexamined Patent Application Publication No. 11-325849
[Patent Document 2] Japanese Unexamined Patent Application Publication No. 2002-139421
[Patent Document 3] Japanese Unexamined Patent Application Publication No. 2003-543
[Patent Document 4] Japanese Unexamined Patent Application Publication No. 2007-24677

DISCLOSURE OF THE INVENTION

Problem that the Invention is to Solve

A number of blood vessels exist in the fundus oculi. The configuration of the blood vessels is important for grasping the condition of the fundus oculi. However, the tomographic image obtained by the fundus oculi observation device does not clearly depict an image region corresponding to the blood vessel (this region includes an underneath region thereof: may be collectively referred to as a vascular region). Therefore, it is impossible to analyze the thickness of the layer in the vascular region with high accuracy.

Since the conventional fundus oculi observation device cannot reflect the position of the blood vessel on the result of the analysis of the layer thickness, it is difficult to grasp which part in the analysis range corresponds to the vascular region. Consequently, in a diagnosis performed with reference to the layer thickness, there is a risk that the precision of the diagnosis is low.

The present invention was made for solving such a problem, and an object of the present invention is to provide a fundus oculi observation device capable of defining which part in the result of analysis of the layer thickness of the fundus oculi is a part having been obtained by analyzing a vascular region, and also provide an opthalmologic image processing device, and a program.

Means for Solving the Above Problem

In order to achieve the abovementioned object, in a first aspect of the present invention, a fundus oculi observation device comprises: a light source configured to output a low-coherence light; an interference-light generator configured to split the low-coherence light into a signal light and a reference light, and superimpose the signal light propagated through a fundus oculi and the reference light propagated through a reference object to generate an interference light; a detector configured to detect the interference light and generate a detection signal; an image forming part configured to form a tomographic image of the fundus oculi based on the detection signal; a calculator configured to calculate layer thickness distribution of the fundus oculi in a cross section of the tomographic image based on the tomographic image; a specifying part configured to specify a vascular region in the tomographic image based on the tomographic image; a display; and a controller configured to control the display to display layer thickness distribution information representing the layer thickness and to also display vascular position information representing a position of the vascular region on the layer thickness distribution information.

Further, in a second aspect of the present invention, the fundus oculi observation device according to the first aspect further comprises an imaging part configured to capture a two-dimensional image of a surface of the fundus oculi, and the device is characterized in that the specifying part is configured to specify the vascular region based on the tomographic image and the two-dimensional image.

Further, in a third aspect of the present invention, the fundus oculi observation device according to the second aspect is characterized in that the specifying part is configured to obtain running position information representing a running position of a blood vessel in the fundus oculi based on the two-dimensional image and specify the vascular region based on the running position information and the tomographic image.

Further, in a fourth aspect of the present invention, the fundus oculi observation device according to the first aspect is characterized in that the controller is configured to display a tomographic image together with the layer thickness distribution information and the vascular position information.

Further, in a fifth aspect of the present invention, the fundus oculi observation device according to the fourth aspect is characterized in that the controller is configured to display the vascular position information displayed on the layer thickness distribution information and the vascular region in the tomographic image so that display positions are associated with each other.

Further, in a sixth aspect of the present invention, the fundus oculi observation device according to the first aspect is characterized in that the controller is configured to display a graph having a horizontal axis defined along the cross section and a vertical axis taking layer thickness values, as the layer thickness distribution information, and display a vascular position image representing a position of the vascular region as the vascular position information.

Further, in a seventh aspect of the present invention, the fundus oculi observation device according to the sixth aspect is characterized in that the controller is configured to display a tomographic image of a display size adjusted to the graph together with the graph, and display the vascular position image at a position on the graph corresponding to the vascular region in the tomographic image.

Further, in an eighth aspect of the present invention, the fundus oculi observation device according to the first aspect is characterized in that: the calculator is configured to specify, based on the tomographic image of the fundus oculi, a predetermined layer position in the tomographic image; and the specifying part is configured to extract a plurality of pixels located in a depth direction of the fundus oculi with respect to a pixel on the predetermined layer position, calculate a statistic representing variation of pixel values of the plurality of pixels, specify such a pixel on the predetermined layer position that the statistic is included in a predetermined range, and specify the vascular region based on the specified pixel.

Further, in a ninth aspect of the present invention, the fundus oculi observation device according to the first aspect is characterized in that: the image forming part is configured to form a plurality of tomographic images at different cross-sectional positions; and the specifying part is configured to accumulate the plurality of tomographic images in a depth direction of the fundus oculi to form an accumulated image, obtain running position information representing a running position of a blood vessel in the fundus oculi based on the accumulated image, and specify the vascular region based on the running position information.

Further, in a tenth aspect of the present invention, the fundus oculi observation device according to the third aspect is characterized in that: the image forming part is configured to form a plurality of tomographic images at different cross-sectional positions; and the specifying part is configured to accumulate the plurality of tomographic images in a depth direction of the fundus oculi to form an accumulated image, execute position matching between the two-dimensional image and the accumulated image, specify, based on a result of the position matching, an image region in the accumulated image corresponding to an image region in the two-dimensional image represented in the running position information, specify a crossing region of the image region in the accumulated image and the cross section of the tomographic image, and set the vascular region so as to include the crossing region.

Further, in an eleventh aspect of the present invention, the fundus oculi observation device according to the first aspect is characterized in that: the image forming part is configured to form a plurality of tomographic images at different cross-sectional positions, and form a tomographic image at a new cross-sectional position based on the plurality of tomographic images; the calculator is configured to calculate layer thickness distribution of the fundus oculi in the new cross section based on the new tomographic image; the specifying part is configured to specify a vascular region in the new tomographic image based on the plurality of tomographic images; and the controller is configured to control to display vascular position information representing a position of the new vascular region on layer thickness distribution information representing the new layer thickness distribution.

Further, in a twelfth aspect of the present invention, the fundus oculi observation device according to the eleventh aspect is characterized in that the controller is configured to display the new tomographic image together with the new layer thickness distribution information and the new vascular region information.

Further, in a thirteenth aspect of the present invention, an opthalmologic image processing device comprises: an accepting part configured to accept a tomographic image of a fundus oculi; a calculator configured to calculate layer thickness distribution of the fundus oculi in a cross section of the tomographic image based on the tomographic image; a specifying part configured to specify a vascular region in the tomographic image based on the tomographic image; a display; and a controller configured to control the display to display layer thickness distribution information representing the layer thickness distribution, and to also display vascular position information representing a position of the vascular region on the layer thickness distribution information.

Further, in a fourteenth aspect of the present invention, a program for causing a computer having an accepting part configured to accept a tomographic image of a fundus oculi and a display to function as: a calculator configured to calculate, based on the tomographic image, layer thickness distribution of the fundus oculi in a cross section of the tomographic image; a specifying part configured to specify a vascular region in the tomographic image based on the tomographic image; and a controller configured to display layer thickness distribution information representing the layer thickness distribution, and also display vascular position information representing a position of the vascular region on the layer thickness distribution information.

EFFECT OF THE INVENTION

According to the present invention, it is possible to, based on a tomographic image of the fundus oculi, calculate layer thickness distribution of the fundus oculi in a cross section of the tomographic image, specify a vascular region in the tomographic image based on the tomographic image, and display layer thickness distribution information representing the layer thickness distribution and also display vascular position information representing the position of the vascular region on the layer thickness distribution information.

Therefore, it is possible to define which part in the result of analysis of the layer thickness of the fundus oculi is a part having been obtained by analyzing the vascular region.

BRIEF DESCRIPTION OF THE DRAWINGS

FIG. 9A shows an example of the scan pattern of the signal light when the fundus oculi is seen from the incident side of the signal light into an eye. FIG. 9B shows an example of an arrangement pattern of scan points on each scan line.

FIG. 10 is a schematic view showing an example of the scan pattern of the signal light and a pattern of a tomographic image formed along each scan line in the embodiment of the fundus oculi observation device according to the present invention.

Figure 1:
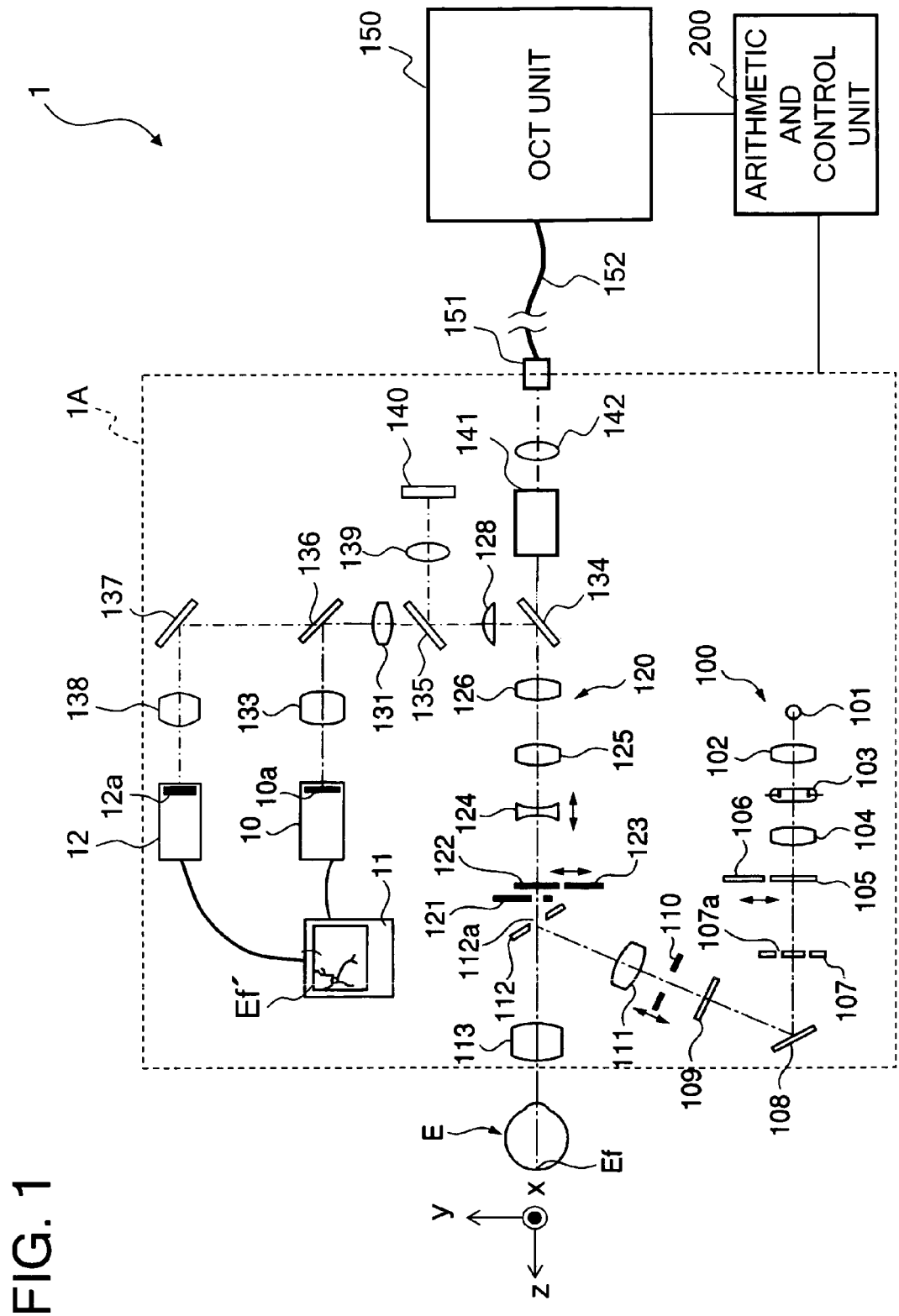
FIG. 1 is a schematic configuration diagram showing an example of the entire configuration of an embodiment of a fundus oculi observation device according to the present invention.

DESCRIPTION OF REFERENCE NUMERALS AND SYMBOLS 1 fundus oculi observation device
1A retinal camera unit
141 scan unit
150 OCT unit
160 low-coherence light source
174 reference mirror
180 spectrometer
184 CCD
200 arithmetic and control unit
210 controller
211 main controller
212 storage
220 image forming part
230 image processor
231 layer thickness distribution calculator
232 layer position specifying part
233 layer thickness calculator
234 vascular region specifying part
240 user interface
240A display
240B manipulation part

BEST MODE FOR CARRYING OUT THE INVENTION

An example of an embodiment of a fundus oculi observation device, an opthalmologic image processing device and a program according to the present invention will be described in detail with reference to the drawings.

The fundus oculi observation device according to the present invention is a device that forms a tomographic image and a three-dimensional image of the fundus oculi by applying the OCT technique.

Furthermore, this fundus oculi observation device has a function of analyzing the layer thickness of the fundus oculi based on the acquired image.

A measurement method applied to this fundus oculi observation device is the Fourier Domain method, the Swept Source method, or the like. In this embodiment, the Fourier Domain type will be described particularly in detail.

Further, the opthalmologic image processing device according to the present invention is a device that analyzes the layer thickness of the fundus oculi based on an image of the fundus oculi acquired by applying the OCT technique. Moreover, the program according to the present invention is for causing a computer to execute an analysis process on the layer thickness of the fundus oculi.

[Entire Configuration]

A fundus oculi observation device 1 shown in FIG. 1 includes a retinal camera unit 1A, an OCT unit 150, and an arithmetic and control unit 200. The retinal camera unit 1A has almost the same optical system as a conventional retinal camera. A retinal camera is a device that captures a two-dimensional image of the fundus oculi surface. The OCT unit 150 houses an optical system for acquiring an OCT image.

The arithmetic and control unit 200 is provided with a computer that executes various kinds of arithmetic processes, control processes, and so on.

To the OCT unit 150, one end of a connection line 152 is attached. To the other end of the connection line 152, a connector part 151 connected to the retinal camera unit 1A is attached. An optical fiber runs through inside the connection line 152. Thus, the OCT unit 150 and the retinal camera unit 1A are optically connected via the connection line 152.

[Configuration of Retinal Camera Unit]

The retinal camera unit 1A has an optical system for forming a two-dimensional image of the fundus oculi surface. Here, a two-dimensional image of the fundus oculi surface represents, for example, a color image, a monochrome image and a fluorescent image (a fluorescein angiography image, an indocyanine green fluorescent image, and so on) obtained by imaging the fundus oculi surface. As well as a conventional retinal camera, the retinal camera unit 1A is provided with an illumination optical system 100 that illuminates a fundus oculi Ef, and an imaging optical system 120 that leads the fundus oculi reflected light of the illumination light to an imaging device 10. The illumination optical system 100 and the imaging optical system 120 are examples of the "imaging part" of the present invention.

The imaging device 10 of the imaging optical system 120 detects an illumination light having a wavelength of near-infrared region, the details of which will be described later. Moreover, the imaging optical system 120 is separately provided with an imaging device 12 that detects an illumination light having a wavelength of visible region.

Furthermore, the imaging optical system 120 acts to lead a signal light coming from the OCT unit 150 to the fundus oculi Ef and also lead the signal light propagated through the fundus oculi Ef to the OCT unit 150.

The illumination optical system 100 includes an observation light source 101, a condenser lens 102, an imaging light source 103, a condenser lens 104, exciter filters 105 and 106, a ring transparent plate 107, a mirror 108, an LCD (Liquid Crystal Display) 109, an illumination diaphragm 110, a relay lens 111, an aperture mirror 112, and an objective lens 113.

The observation light source 101 outputs an illumination light having a wavelength of visible region included in the range of about 400-700 nm, for example. On the other hand, the imaging light source 103 outputs an illumination light having a wavelength of near-infrared region included in the range of about 700-800 nm, for example. The near-infrared light outputted from the imaging light source 103 is set so as to have a shorter wavelength than a light used by the OCT unit 150 (described later).

Further, the imaging optical system 120 includes the objective lens 113, (an aperture 112a of) the aperture mirror 112, an imaging diaphragm 121, barrier filters 122 and 123, a magnifying lens 124, a relay lens 125, an imaging lens 126, a dichroic mirror 134, a field lens 128, a half mirror 135, a relay lens 131, a dichroic mirror 136, an imaging lens 133, the imaging device 10 (an image pick-up element 10a), a reflection mirror 137, an imaging lens 138, the imaging device 12 (an image pick-up element 12a), a lens 139, and an LCD 140.

Furthermore, the imaging optical system 120 is provided with the dichroic mirror 134, the half mirror 135, the dichroic mirror 136, the reflection mirror 137, the imaging lens 138, the lens 139, and the LCD 140.

The dichroic mirror 134 is configured to reflect the fundus oculi reflected light (having a wavelength included in the range of about 400-800 nm) of the illumination light coming from the illumination optical system 100, and to transmit a signal light LS (having a wavelength included in the range of about 800-900 nm, for example; described later) coming from the OCT unit 150.

Further, the dichroic mirror 136 is configured to transmit the illumination light having a wavelength of visible region coming from the illumination optical system 100 (a visible light having a wavelength of about 400-700 nm outputted from the observation light source 101), and to reflect the illumination light having a wavelength of near-infrared region (a near-infrared light having a wavelength of about 700-800 nm outputted from the imaging light source 103).

The LCD 140 displays a fixation target (an internal fixation target) for fixing an eye E. After focused by the lens 139, the light from the LCD 140 is reflected by the half mirror 135, propagated through the field lens 128, and reflected by the dichroic mirror 136.

Furthermore, this light is propagated through the imaging lens 126, the relay lens 125, the magnifying lens 124, the (aperture 112a of the) aperture mirror 112, the objective lens 113 and so on, and enters the eye E. Consequently, an internal fixation target is projected onto the fundus oculi Ef of the eye E.

The image pick-up element 10a is an image pick-up element such as a CCD (Charge Coupled Device) or a CMOS (Complementary Metal Oxide Semiconductor) installed in the imaging device 10 such as a TV camera, and specifically detects a light having a wavelength of near-infrared region. In other words, the imaging device 10 is an infrared TV camera that detects a near-infrared light. The imaging device 10 outputs a video signal as the result of detection of the near-infrared light.

A touch panel monitor 11 displays a two-dimensional image (a fundus oculi image Ef') of the surface of the fundus oculi Ef based on the video signal. Moreover, this video signal is sent to the arithmetic and control unit 200, and the fundus oculi image is displayed on a display (described later).

For imaging by the imaging device 10, for example, an illumination light having a wavelength of near-infrared region outputted from the imaging light source 103 is used.

On the other hand, the image pick-up element 12a is an image pick-up element such as a CCD or a CMOS installed in the imaging device 12 such as a TV camera, and specifically detects a light having a wavelength of visible region. In other words, the imaging device 12 is a TV camera that detects a visible light. The imaging device 12 outputs a video signal as the result of detection of the visible light.

The touch panel monitor 11 displays a two-dimensional image (the fundus oculi image Ef) of the surface of the fundus oculi Ef based on the video signal. Moreover, this video signal is sent to the arithmetic and control unit 200, and the fundus oculi image is displayed on the display (described later).

For imaging the fundus oculi by the imaging device 12, for example, an illumination light having a wavelength of visible region outputted from the observation light source 101 is used.

The retinal camera unit 1A is provided with a scan unit 141 and a lens 142. The scan unit 141 scans a radiation position on the fundus oculi Ef of a light (the signal light LS; described later) outputted from the OCT unit 150.

The lens 142 collimates the signal light LS led from the OCT unit 150 through the connection line 152, and makes the light enter the scan unit 141. Further, the lens 142 focuses the fundus oculi reflected light of the signal light LS propagated through the scan unit 141.

Figure 2:
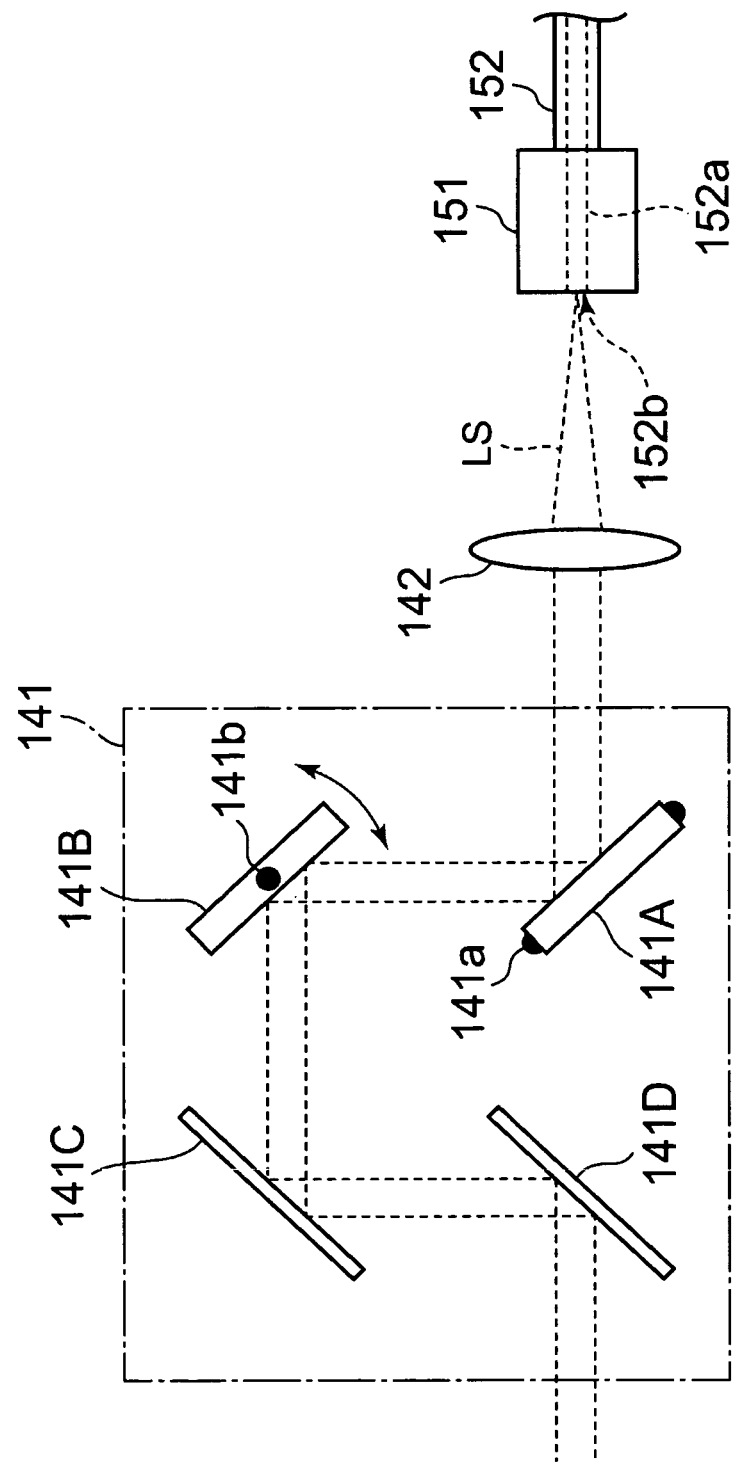
FIG. 2 is a schematic configuration diagram showing an example of the configuration of a scan unit installed in a retinal camera unit in the embodiment of the fundus oculi observation device according to the present invention.

FIG. 2 shows an example of the configuration of the scan unit 141. The scan unit 141 includes Galvano mirrors 141A and 141B, and reflection mirrors 141C and 141D.

The Galvano mirrors 141A and 141B are reflection mirrors arranged so as to be rotatable about rotary shafts 141a and 141b, respectively. The respective Galvano mirrors 141A and 141B are rotated about the rotary shafts 141a and 141b by drive mechanisms described later (mirror drive mechanisms 241 and 242 shown in FIG. 5).

Consequently, the directions of the reflection surfaces (surfaces to reflect the signal light LS) of the respective Galvano mirrors 141A and 141B are changed.

The rotary shafts 141a and 141b are arranged orthogonally to each other. In FIG. 2, the rotary shaft 141a of the Galvano mirror 141A is arranged in the parallel direction to the paper surface. On the other hand, the rotary shaft 141b of the Galvano mirror 141B is arranged in the orthogonal direction to the paper surface.

That is to say, the Galvano mirror 141B is configured to be rotatable in the direction indicated by an arrow pointing to both directions in FIG. 2, whereas the Galvano mirror 141A is configured to be rotatable in the direction orthogonal to the arrow pointing to both the directions. Consequently, the Galvano mirrors 141A and 141B act to change the reflection directions of the signal light LS into directions orthogonal to each other, respectively. As apparent from FIGS. 1 and 2, a scan with the signal light LS is performed in the x-direction when the Galvano mirror 141A is rotated, and a scan with the signal light LS is performed in the y-direction when the Galvano mirror 141B is rotated.

The signal light LS reflected by the Galvano mirrors 141A and 141B is reflected by the reflection mirrors 141C and 141D, and travels in the same direction as having entered the Galvano mirror 141A.

An end surface 152b of an optical fiber 152a inside the connection line 152 is arranged so as to face the lens 142. The signal light LS emitted from the end surface 152b travels while expanding the beam diameter thereof toward the lens 142, and is collimated by the lens 142. On the contrary, the signal light LS propagated through the fundus oculi Ef is focused to the end surface 152b by the lens 142, and enters the optical fiber 152a.

[Configuration of OCT Unit]

Next, the configuration of the OCT unit 150 will be described with reference to FIG. 3. The OCT unit 150 has an optical system for forming an OCT image of the fundus oculi.

The OCT unit 150 is provided with an optical system almost the same as that of a conventional Fourier-Domain-type optical image measurement device. That is to say, the OCT unit 150 splits a low-coherence light into a reference light and a signal light, superimposes the signal light propagated through an eye and the reference light propagated through a reference object to generate an interference light, and detects this interference light. This detection result (a detection signal) is inputted into the arithmetic and control unit 200. The arithmetic and control unit 200 analyzes this detection signal and forms a tomographic image or a three-dimensional image of the fundus oculi.

A low-coherence light source 160 is composed of a broadband light source that outputs a low-coherence light L0. For example, a super luminescent diode (SLD), a light emitting diode (LED) or the like is used as the broadband light source. The low-coherence light source 160 is an example of the "light source" of the present invention.

The low-coherence light L0 is, for example, a light that includes a light having a wavelength of near-infrared region and that has a temporal coherence length of about several tens of micrometers. The low-coherence light L0 has a longer wavelength than the illumination light (having a wavelength of about 400-800 nm) of the retinal camera unit 1A, for example, a wavelength included in the range of about 800-900 nm.

The low-coherence light L0 outputted from the low-coherence light source 160 is led to an optical coupler 162 through an optical fiber 161. The optical fiber 161 is composed of, for example, a single mode fiber, a PM (polarization maintaining) fiber or the like. The optical coupler 162 splits the low-coherence light L0 into a reference light LR and the signal light LS.

The optical coupler 162 acts as both a part for splitting a light (a splitter) and a part for superposing lights (a coupler), but will be herein referred to as an "optical coupler" idiomatically.

The reference light LR generated by the optical coupler 162 is led by an optical fiber 163 composed of a single mode fiber or the like, and is emitted from the end surface of the fiber. Furthermore, after collimated by a collimator lens 171, the reference light LR is propagated through a glass block 172 and a density filter 173, and reflected by a reference mirror 174. The reference mirror 174 is an example of the "reference object" of the present invention.

The reference light LR reflected by the reference mirror 174 is again propagated through the density filter 173 and the glass block 172, focused to the fiber end surface of the optical fiber 163 by the collimator lens 171, and led to the optical coupler 162 through the optical fiber 163.

Here, the glass block 172 and the density filter 173 act as a delaying part for matching the optical path lengths (the optical distances) of the reference light LR and the signal light LS, and also as a dispersion compensating part for matching the dispersion properties of the reference light LR and the signal light LS.

Further, the density filter 173 also acts as a neutral density filter that reduces the light amount of the reference light LR. The density filter 173 is composed of, for example, a rotary-type ND (Neutral Density) filter. The density filter 173 is driven to rotate by a drive mechanism (a density-filter drive mechanism 244 described later; refer to FIG. 5) including a driver such as a motor. Consequently, the light amount of the reference light LR contributing to generation of the interference light LD is changed.

Figure 3:
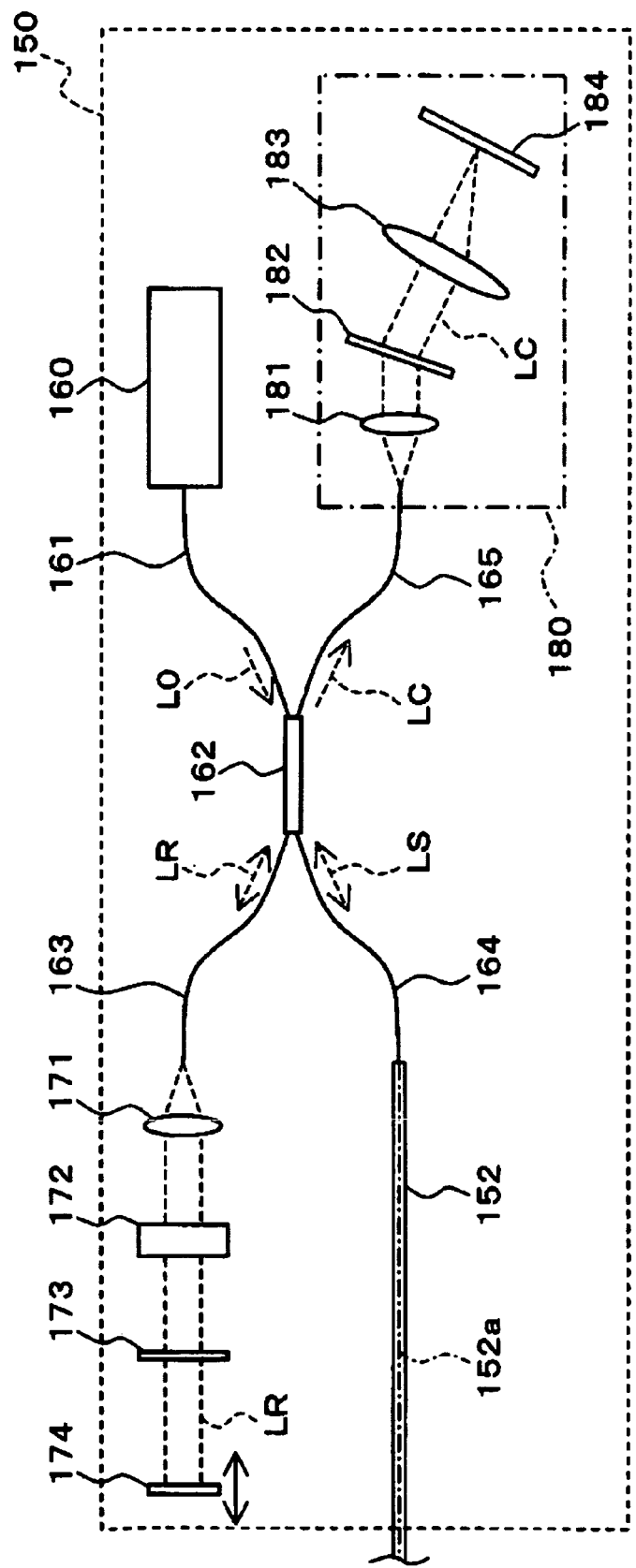
FIG. 3 is a schematic configuration diagram showing an example of the configuration of an OCT unit in the embodiment of the fundus oculi observation device according to the present invention.

Further, the reference mirror 174 is configured to be movable in the traveling direction of the reference light LR (a direction of an arrow pointing to both sides shown in FIG. 3). Thus, it is possible to ensure an optical path length of the reference light LR according to the axial length of the eye E, a working distance (a distance between the objective lens 113 and the eye E), and so on. Moreover, by moving the reference mirror 174, it is possible to acquire an image at an arbitrary depth position of the fundus oculi Ef. The reference mirror 174 is moved by a drive mechanism (a reference-mirror drive mechanism 243 described later; refer to FIG. 5) including a driver such as a motor.

On the other hand, the signal light LS generated by the optical coupler 162 is led to the end part of the connection line 152 through an optical fiber 164 composed of a single mode fiber or the like. The optical fiber 152a runs through inside the connection line 152. Here, the optical fiber 164 and the optical fiber 152a may be composed of a single optical fiber, or may be integrally formed by joining the end surfaces of the respective fibers, for example. Anyway, it is sufficient as far as the optical fibers 164 and 152a are configured to be capable of transmitting the signal light LS between the retinal camera unit 1A and the OCT unit 150.

The signal light LS is led through the inside of the connection line 152 and guided to the retinal camera unit 1A. Furthermore, the signal light LS is propagated through the lens 142, the scan unit 141, the dichroic mirror 134, the imaging lens 126, the relay lens 125, the magnifying lens 124, the imaging diaphragm 121, the aperture 112a of the aperture mirror 112 and the objective lens 113, and radiated to the eye E. For radiating the signal light LS to the eye E, the barrier filters 122 and 123 are previously retracted from the optical path, respectively.

The signal light LS having entered the eye E is formed into an image on the fundus oculi Ef and then reflected. At this moment, the signal light LS not only is reflected by the surface of the fundus oculi Ef but also reaches a deep region of the fundus oculi Ef to be scattered at the refractive index boundary. Therefore, the signal light LS propagated through the fundus oculi Ef contains information reflecting the surface morphology of the fundus oculi Ef and information reflecting the state of backscatter at the refractive index boundary of deep layer tissues of the fundus oculi Ef. This light may be simply referred to as the "fundus oculi reflected light of the signal light LS."

The fundus oculi reflected light of the signal light LS travels reversely on the abovementioned path in the retinal camera unit 1A to be focused to the end surface 152b of the optical fiber 152a, enters the OCT unit 150 through the optical fiber 152a, and returns to the optical coupler 162 through the optical fiber 164.

The optical coupler 162 superimposes the signal light LS having returned through the eye E and the reference light LR reflected by the reference mirror 174 to generate an interference light LC. This interference light LC is led to a spectrometer 180 through an optical fiber 165 composed of a single mode fiber or the like.

Although a Michelson-type interferometer is employed in this embodiment, it is possible to properly employ an arbitrary type of interferometer such as the Mach-Zehnder-type.

The "interference-light generator" of the present invention includes, for example, the optical coupler 162, an optical member on the optical path of the signal light LS (namely, an optical member placed between the optical coupler 162 and the eye E), and an optical member on the optical path of the reference light LR (namely, an optical member placed between the optical coupler 162 and the reference mirror 174). To be specific, the interference-light generator includes an interferometer provided with the optical coupler 162, the optical fibers 163 and 164 and the reference mirror 174.

The spectrometer 180 includes a collimator lens 181, a diffraction grating 182, an image forming lens 183, and a CCD 184.

The diffraction grating 182 may be a transmission-type diffraction grating that transmits light, or may be a reflection-type diffraction grating that reflects light. Moreover, it is also possible to use another photodetecting device such as a CMOS device, instead of the CCD 184.

The interference light LC having entered the spectrometer 180 is collimated by the collimator lens 181, and divided into spectra by the diffraction grating 182 (spectral resolution). The divided interference light LC are formed into an image on the image pick-up surface of the CCD 184 by the image forming lens 183. The CCD 184 detects the respective spectral components of the divided interference light LC and converts the components into electric charges. The CCD 184 accumulates the electric charges and generates a detection signal.

Furthermore, the CCD 184 transmits this detection signal to the arithmetic and control unit 200. The time and timing of accumulation of the electric charges and the timing of transmission of the detection signal are controlled by the arithmetic and control unit 200, for example. The CCD 184 is an example of the "detector" of the present invention.

[Configuration of Arithmetic and Control Unit]

Next, the configuration of the arithmetic and control unit 200 will be described. The arithmetic and control unit 200 analyzes the detection signal inputted from the CCD 184 of the OCT unit 150, and forms an OCT image of the fundus oculi Ef. A method of this analysis is the same as in the conventional Fourier-Domain-OCT technique.

Further, the arithmetic and control unit 200 forms a two-dimensional image showing the morphology of the surface of the fundus oculi Ef based on the video signals outputted from the imaging devices 10 and 12 of the retinal camera unit 1A.

Furthermore, the arithmetic and control unit 200 controls each part of the retinal camera unit 1A and the OCT unit 150.

The arithmetic and control unit 200 executes control of the retinal camera unit 1A such as: control of output of the illumination lights by the observation light source 101 and the imaging light source 103; control of insertion/retraction of the exciter filters 105, 106 and the barrier filters 122, 123 to/from the optical path; control of the operation of a display device such as the LCD 140; control of movement of the illumination diaphragm 110 (control of the diaphragm value); control of the diaphragm value of the imaging diaphragm 121; and control of movement of the magnifying lens 124 (control of the magnification). Furthermore, the arithmetic and control unit 200 executes control of the operation of the Galvano mirrors 141A and 141B.

On the other hand, the arithmetic and control unit 200 executes control of the OCT unit 150 such as: control of output of the low-coherence light L0 by the low-coherence light source 160; control of movement of the reference mirror 174; control of the rotation operation of the density filter 173 (the operation of changing the reduction amount of the light amount of the reference light LR); and control of the timing of accumulation and the timing of output of signals by the CCD 184.

Figure 4:
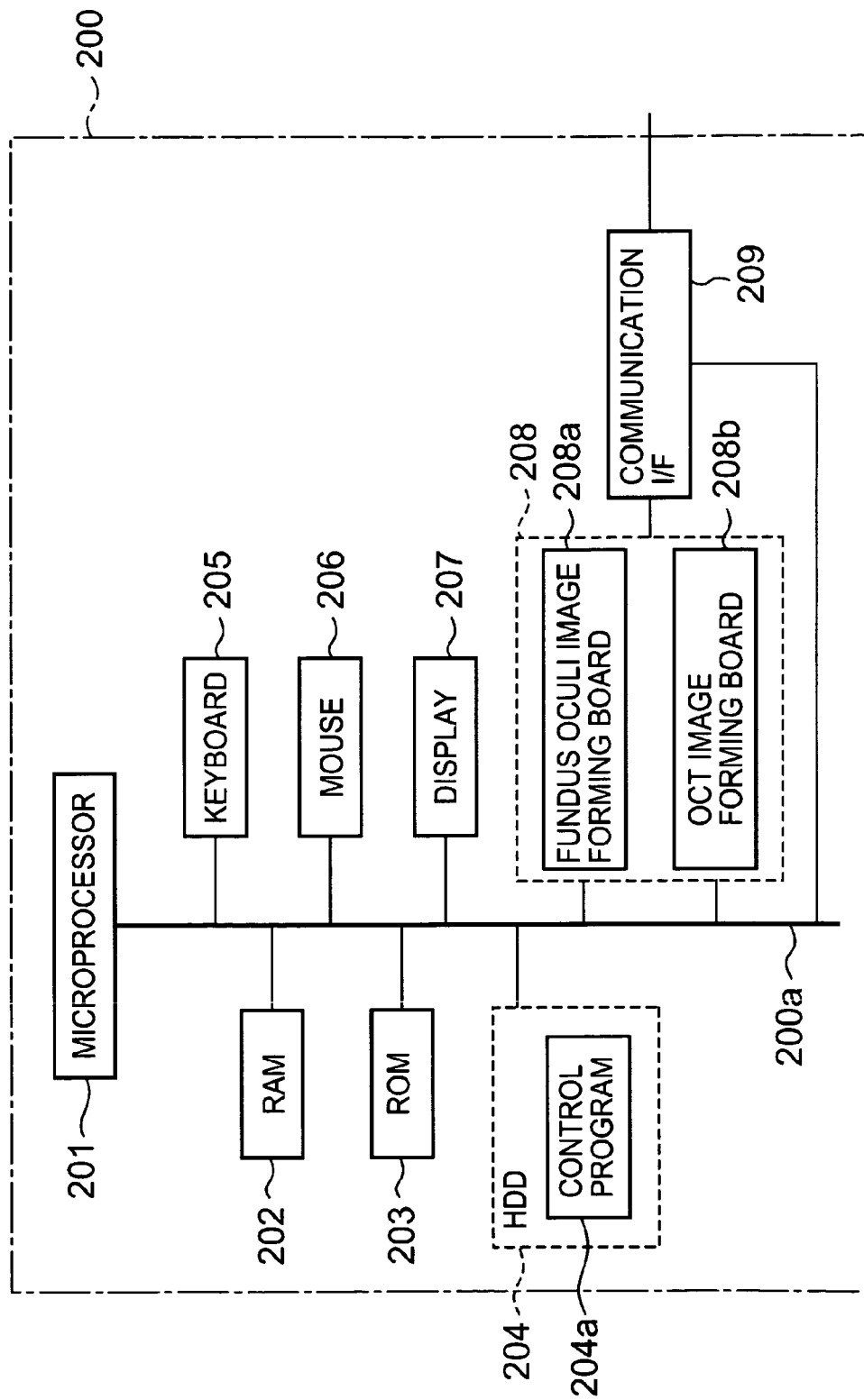
FIG. 4 is a schematic block diagram showing an example of the hardware configuration of an arithmetic and control unit in the embodiment of the fundus oculi observation device according to the present invention.

The hardware configuration of this arithmetic and control unit 200 will be described with reference to FIG. 4.

The arithmetic and control unit 200 is provided with a similar hardware configuration to that of a conventional computer. To be specific, the arithmetic and control unit 200 includes a microprocessor 201, a RAM 202, a ROM 203, a hard disk drive (HDD) 204, a keyboard 205, a mouse 206, a display 207, an image forming board 208, and a communication interface (I/F) 209. The respective parts are connected by a bus 200a.

The microprocessor 201 includes a CPU (Central Processing Unit), an MPU (Micro Processing unit) or the like. The microprocessor 201 reads out a control program 204a from the hard disk drive 204 and loads the program onto the RAM 202, thereby causing the fundus oculi observation device 1 to execute an operation characteristic to the present embodiment.

Further, the microprocessor 201 executes control of each of the aforementioned parts of the device, various kinds of arithmetic processes, and so on. Moreover, the microprocessor 201 receives a manipulation signal from the keyboard 205 or the mouse 206 and, in accordance with the content of the manipulation, controls each of the parts of the device. Furthermore, the microprocessor 201 executes control of a display process by the display 207, control of a process of transmission/reception of data and signals by the communication interface 209, and so on.

The keyboard 205, the mouse 206, and the display 207 are used as user interfaces of the fundus oculi observation device 1. For example, the keyboard 205 is used as a device for typing letters, figures or the like. The mouse 206 is used as a device for performing various kinds of manipulations for input into the display screen of the display 207.

Further, the display 207 is a display device such as an LCD or a CRT (Cathode Ray Tube) display, and displays various kinds of images such as an image of the fundus oculi Ef formed by the fundus oculi observation device 1, and also displays various kinds of screens such as a manipulation screen and a set-up screen.

The user interface of the fundus oculi observation device 1 is not limited to such a configuration, and may include, for example, a trackball, a joystick, a touch-panel LCD, and a control panel for opthalmologic examination. As the user interface, it is possible to employ an arbitrary configuration provided with a function of displaying/outputting information and a function of inputting information and manipulating the device.

The image forming board 208 is a dedicated electronic circuit that executes a process of forming (image data of) an image of the fundus oculi Ef. The image forming board 208 is provided with a fundus oculi image forming board 208a and an OCT image forming board 208b.

The fundus oculi image forming board 208a is a dedicated electronic circuit that forms image data of a fundus oculi image based on video signals from the imaging device 10 and the imaging device 12.

On the other hand, the OCT image forming board 208b is a dedicated electronic circuit that forms image data of a tomographic image of the fundus oculi Ef based on a detection signal from the CCD 184 of the OCT unit 150.

By installing this image forming board 208, it is possible to increase the processing speed for the process of forming a fundus oculi image and a tomographic image.

The communication interface 209 transmits control signals from the microprocessor 201, to the retinal camera unit 1A or the OCT unit 150. Moreover, the communication interface 209 receives video signals from the imaging devices 10 and 12 and a detection signal from the CCD 184 of the OCT unit 150, and inputs the signals into the image forming board 208. At this moment, the communication interface 209 inputs the video signals from the imaging devices 10 and 12, into the fundus oculi image forming board 208a, and inputs the detection signal from the CCD 184, into the OCT image forming board 208b.

Further, in a case that the arithmetic and control unit 200 is connected to a communication line such as a LAN (Local Area Network) or the Internet, it is possible to provide the communication interface 209 with a network adapter such as a LAN card or communication equipment such as a modem, thereby configuring to be capable of data communication via this communication network. In this case, it is possible to install a server that stores the control program 204a to the communication network and configure the arithmetic and control unit 200 as a client terminal of the server, thereby causing the fundus oculi observation device 1 to operate.

[Configuration of Control System]

Figure 5:
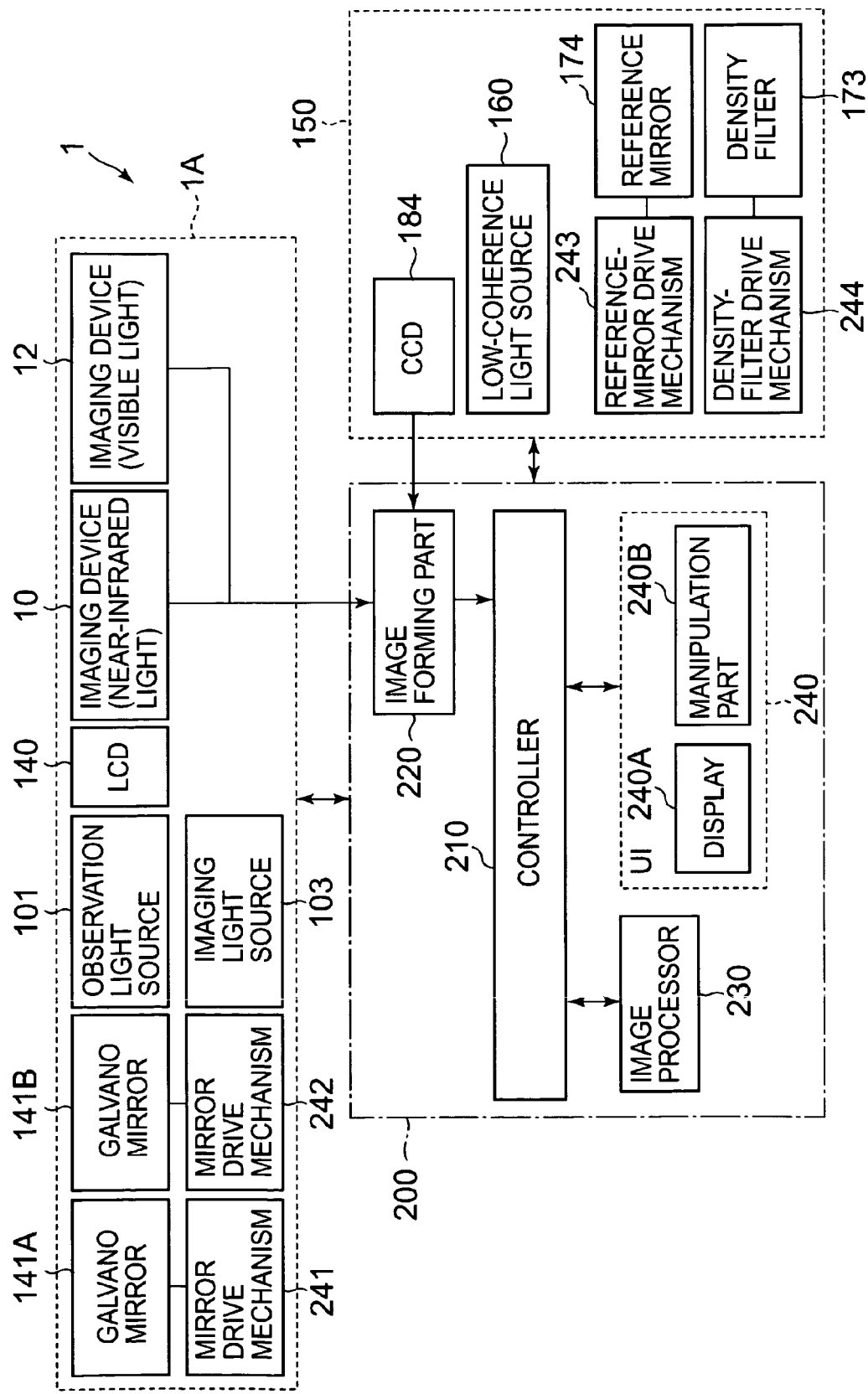
FIG. 5 is a schematic block diagram showing an example of the configuration of a control system in the embodiment of the fundus oculi observation device according to the present invention.
Figure 6:
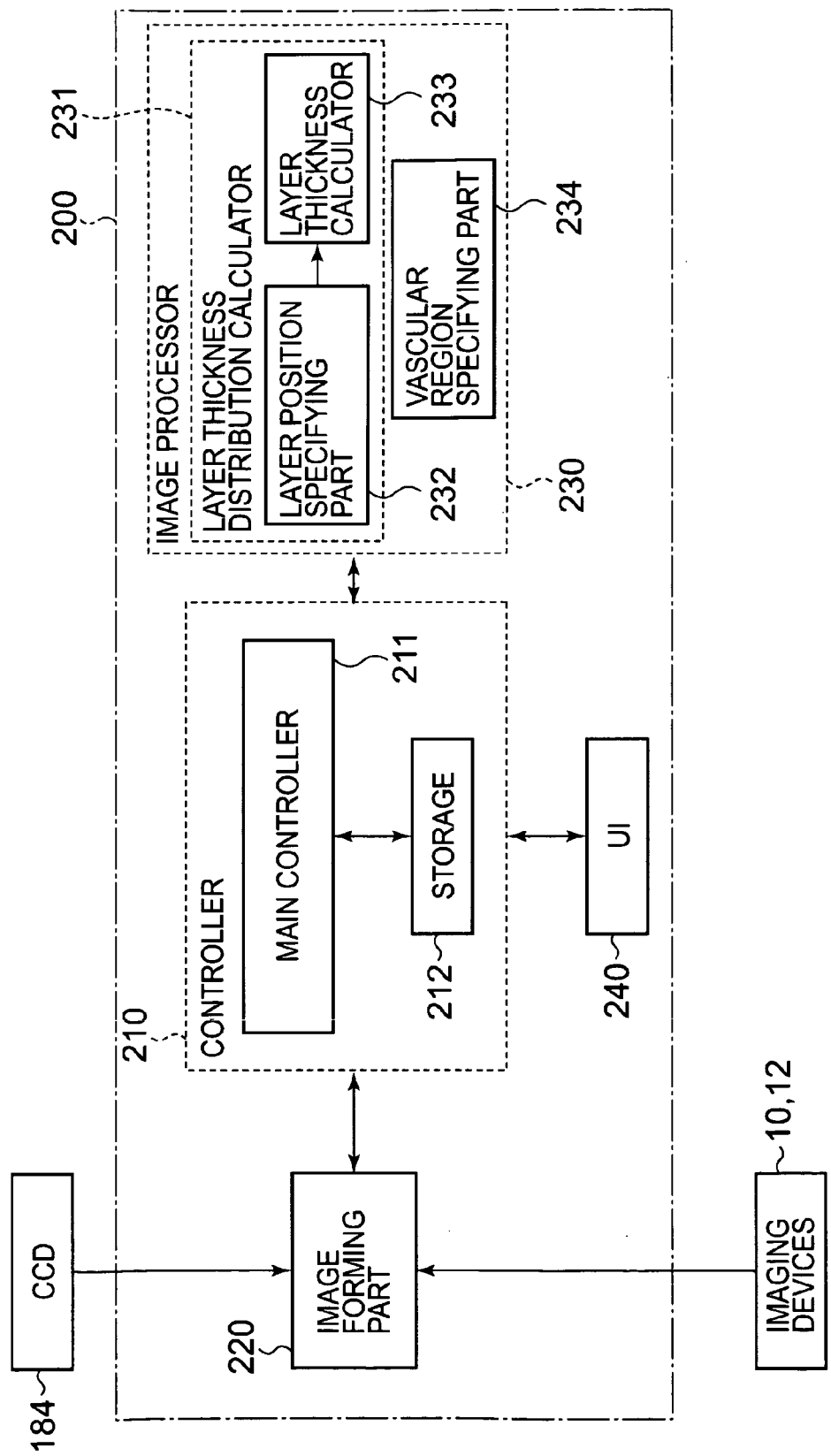
FIG. 6 is a schematic block diagram showing an example of the configuration of a control system in the embodiment of the fundus oculi observation device according to the present invention.

Next, the configuration of a control system of the fundus oculi observation device 1 will be described with reference to FIGS. 5 and 6.

(Controller)

The control system of the fundus oculi observation device 1 is configured mainly by a controller 210 of the arithmetic and control unit 200. The controller 210 includes the microprocessor 201, the RAM 202, the ROM 203, the hard disk drive 204 (the control program 204a), the communication interface 209, and so on. The controller 210 is an example of the "controller" of the present invention.

The controller 210 is provided with a main controller 211 and a storage 212. The main controller 211 executes the aforementioned various kinds of controls.

The storage 212 stores various kinds of data. The data stored in the storage 212 is, for example, the image data of an OCT image, the intensity of a detection signal (the intensity of each frequency component), subject information (information on a subject such as the patient ID and name), and so on. The main controller 211 executes a process of writing the data into the storage 212, and a process of reading out the data from the storage 212.

(Image Forming Part)

An image forming part 220 forms the image data of the fundus oculi images Ef' based on the video signals from the imaging devices 10 and 12.

Further, the image forming part 220 forms the image data of a tomographic image of the fundus oculi Ef based on the detection signal from the CCD 184. This process includes, for example, noise elimination (noise reduction), filtering, FFT (Fast Fourier Transform), and so on. For example, the image forming part 220 determines the pixel value (the luminance value) based on the intensity of a detection signal, more specifically, the intensities of frequency components, thereby forming the image data of a tomographic image.

The image forming part 220 includes the image forming board 208, the communication interface 209, and so on. In this specification, "image data" and an "image" displayed based thereon may be identified with each other.

(Image Processor)

An image processor 230 executes various kinds of image processing and analysis processes on the image data of an image formed by the image forming part 220. For example, the image processor 230 executes various kinds of correction processes such as luminance correction and dispersion correction of an image.

Further, the image processor 230 executes an interpolation process of interpolating pixels between tomographic images formed by the image forming part 220, thereby forming the image data of a three-dimensional image of the fundus oculi Ef.

The image data of a three-dimensional image means such image data that the positions of the pixels are defined by the three-dimensional coordinates. An example of the image data of a three-dimensional image is image data composed of three-dimensionally arranged voxels. This image data is referred to as volume data, voxel data, or the like. For displaying an image based on volume data, the image processor 230 executes a rendering process (such as volume rendering and MIP (Maximum Intensity Projection)) on this volume data, and forms the image data of a pseudo three-dimensional image taken from a specified view direction. On a display device such as the display 207, a pseudo three-dimensional image based on this image data is displayed.

Further, it is also possible to form stack data of a plurality of tomographic images as the image data of a three-dimensional image.

Stack data is image data obtained by three-dimensionally arranging a plurality of tomographic images obtained along a plurality of scan lines, based on the positional relation of the scan lines.

Further, the image processor 230 is capable of forming a tomographic image with an arbitrary position of the fundus oculi Ef as a cross section, based on the image data of the three-dimensional image of the fundus oculi Ef. For example, it is possible to execute this process by selecting pixels crossing the cross section described above from among pixels of the image data of the three-dimensional image, and forming image data. An image displayed based on this image data is the tomographic image in the cross section described above.

(Layer Thickness Distribution Calculator)

A layer thickness distribution calculator 231 analyzes a tomographic image of the fundus oculi Ef and obtains the distribution of the thicknesses of the layers of the fundus oculi Ef. The layer thickness distribution calculator 231 is an example of the "calculator" of the present invention.

For example, the layer thickness distribution calculator 231 specifies the positions of the layers in the tomographic image and calculates the distance between the layers to obtain layer thickness, and arranges the acquisition results of the layer thicknesses in accordance with the analyzed positions to obtain the layer thickness distribution. For this purpose, the layer thickness distribution calculator 231 is provided with a layer position specifying part 232 and a layer thickness calculator 233.

(Layer Position Specifying Part)

The layer position specifying part 232 specifies the positions of the layers in the tomographic image. For this purpose, the layer position specifying part 232 firstly executes preprocessing for making it easy to obtain the layer positions in the tomographic image as needed. As the preprocessing, for example, image processing such as a tone conversion process, an image enhancement process, a threshold process, a contrast conversion process, a binarizing process, an edge detection process, an image averaging process, an image smoothing process and a filtering process is executed. The abovementioned image processing can be executed properly in combination.

Next, the layer position specifying part 232 analyzes the pixel values (for example, the luminance values) of pixels composing the tomographic image, for each line along the depth direction of the fundus oculi Ef.

To be specific, a tomographic image to be analyzed is composed of a plurality of depthwise images arranged along a predetermined cross section (refer to an image Gij shown in FIG. 10). The layer position specifying part 232 sequentially refers to the pixel values of the pixels composing the depthwise images sequentially along the depth direction, thereby specifying pixels corresponding to the boundary position of the adjacent layers. This process can be executed by using a filter extending only in the depth direction (a line filter such as a differential filter), or a filter extending in the depth direction and the direction orthogonal thereto (an area filter). These filters are previously stored in the hard disk drive 204, for example.

Thus, the layer position specifying part 232 obtains an image region corresponding to the boundary position between the layers, and also obtains an image region corresponding to the layer. Since the fundus oculi Ef is formed in a manner that a plurality of layers are stacked, specification of a layer is synonymous with specification of the boundary position of layers.

As mentioned before, the fundus oculi Ef has the retina, the choroidea and the sclera in order from the fundus oculi surface side in the depth direction. Moreover, the retina has the internal limiting membrane, the nerve fiber layer, the ganglion cell layer, the inner plexiform layer, the inner nuclear layer, the outer plexiform layer, the outer nuclear layer, the external limiting membrane, the photoreceptor cell layer and the retinal pigment epithelium layer in order from the fundus oculi surface side in the depth direction. The layer position specifying part 232 specifies the position of at least one of these layers (the boundary position between the layers).

To be specific, the layer position specifying part 232 specifies the IS/OS position (the boundary position between the inner nuclear layer and the outer plexiform layer). It is possible to specify the IS/OS position by extracting the inner nuclear layer and the outer plexiform layer, and specifying the boundary position therebetween as the IS/OS position. Alternatively, it is possible to specify the IS/OS position by change of the luminance value of the tomographic image.

Alternatively, it is possible to specify the IS/OS position with reference to the distance from a reference position (the fundus oculi surface, the retinal pigment epithelium layer, or the like) in a tomographic image.

The "layer" includes the abovementioned layers composing the retina, and also includes the choroidea, the sclera, the external tissues thereof, and so on. Moreover, the boundary position between the layers includes the abovementioned boundary position of the layers composing the retina, and also includes the boundary position between the internal limiting membrane and the vitreous body, the boundary position between the retinal pigment epithelium layer and the choroidea, the boundary position between the choroidea and sclera, the boundary position between the sclera and the external tissues thereof, and so on.

(Layer Thickness Calculator)

The layer thickness calculator 233 executes a process of calculating the thickness of a predetermined site of the fundus oculi Ef based on the position of the layer specified by the layer position specifying part 232.

Here, the predetermined site of the fundus oculi Ef means one or more layers among a plurality of layers of the fundus oculi Ef described above. For example, the "predetermined site" may be only the retinal pigment epithelium layer, or may be a plurality of layers from the internal limiting membrane to the inner nuclear layer.

Further, the thickness of the "predetermined site" to be calculated is, for example, the thickness from the internal limiting membrane to the nerve fiber layer (the nerve fiber layer thickness), the thickness from the internal limiting membrane to the inner nuclear layer (the IS/OS position of the photoreceptor cell) (the retina thickness), the thickness from the internal limiting membrane to the retinal pigment epithelium layer (the retina thickness), and so on.

Among these three examples, the second and third examples represent the retina thickness though the definitions thereof are different.

An example of the process executed by the layer thickness calculator 233 will be described. As mentioned before, the layer position specifying part 232 specifies the position (the boundary positions) of a layer of the fundus oculi Ef in a tomographic image. At this moment, at least two boundary positions are specified (namely, at least one layer). The layer thickness calculator 233 calculates the distance between predetermined two boundary positions among the specified boundary positions.

To be specific, the layer thickness calculator 233 calculates the distance (the depthwise distance) between pixels corresponding to the two boundary positions in the respective depthwise images composing the tomographic image. Here, coordinate values of the xyz coordinate system mentioned above are assigned to the respective pixels of the depthwise image (the x-coordinate value and the y-coordinate value are constant, respectively). The layer thickness calculator 233 is capable of calculating the distance between the pixels based on these coordinate values. Alternatively, the layer thickness calculator 233 can also calculate the intended distance based on the number of pixels between the pixels corresponding to the two boundary positions and based on the distance (known) between the adjacent pixels.

Based on the thicknesses of a layer at a plurality of positions of the fundus oculi Ef acquired by the layer thickness calculator 233, the layer thickness distribution calculator 231 generates information representing the distribution of the thicknesses of this layer (the layer thickness distribution information). The layer thickness distribution information is, for example, a layer thickness graph that graphs the distribution of the thicknesses of the layer in a predetermined cross-sectional position. Alternatively, as the layer thickness distribution information, a layer thickness distribution image that represents the one-dimensional or two-dimensional distribution of the thicknesses of the layer in color corresponding to the thicknesses of the layer may be applied.

The process of generating the layer thickness distribution information will be described more specifically. The information acquired by the layer thickness calculator 233 is information that relates the analysis position of the layer thickness and the value of the layer thickness. That is to say, as described above, the layer thickness is obtained for each depthwise image, and coordinate values of the xyz coordinate system (or the xy coordinate system) are assigned to each depthwise image. Accordingly, the layer thickness calculator 233 is capable of relating the analysis position defined by the xyz coordinate system (or the xy coordinate system) and the value of the layer thickness calculated based on the depthwise image at this analysis position.

The layer thickness distribution calculator 231 is capable of generating the layer thickness distribution information by arranging, for example, in accordance with the analysis position, the information that relates the analysis position with the value of the layer thickness.

Further, the layer thickness distribution calculator 231 is capable of generating the layer thickness graph by selecting information included in a predetermined cross-sectional position (the position is defined by the xyz coordinate system or xy coordinate system) from among the information acquired by the layer thickness calculator 233, and arranging the values of the layer thicknesses of the selected information in accordance with the analysis positions. For example, by defining the analysis positions on the horizontal axis and plotting the values of the layer thicknesses on the vertical axis based on the thus generated information, it is possible to display this layer thickness graph. This display process is executed by the main controller 211.

Further, the layer thickness distribution calculator 231 is capable of generating the layer thickness distribution image (image data) by selecting information included in a predetermined region (the position is defined by the xyz coordinate system or xy coordinate system) from among the information acquired by the layer thickness calculator 233, arranging the values of the layer thicknesses of the selected information in accordance with the analysis positions, and also assigning colors corresponding to the values of the layer thicknesses. By displaying the respective pixels within the predetermined region in the assigned colors based on the thus generated image data, it is possible to display the layer thickness distribution image. This display process is executed by the main controller 211.

(Vascular Region Specifying Part)

A vascular region specifying part 234 of the image processor 230 specifies a vascular region in a tomographic image of the fundus oculi Ef. The vascular region specifying part 234 is an example of the "specifying part" of the present invention.

Here, the vascular region may include, in addition to an image region corresponding to a fundus blood vessel, an image region located below the abovementioned image region (in the z-direction shown in FIG. 1). That is to say, the vascular region can be an image region corresponding to the position of a blood vessel when the fundus oculi is seen from the cornea side of the eye E. In other words, in a case that a blood vessel has coordinate values (x,y,z) in the xyz coordinate system, the position of the vascular region can be expressed by coordinate values (x,y) obtained by projecting the coordinate values (x,y,z) to the xy plane.

The vascular region will be described with reference to FIG. 7. A tomographic image G of the fundus oculi Ef shown in FIG. 7 depicts layer regions L1, L2 and L3 and boundary regions g1, g2, g3 and g4.

Figure 7:
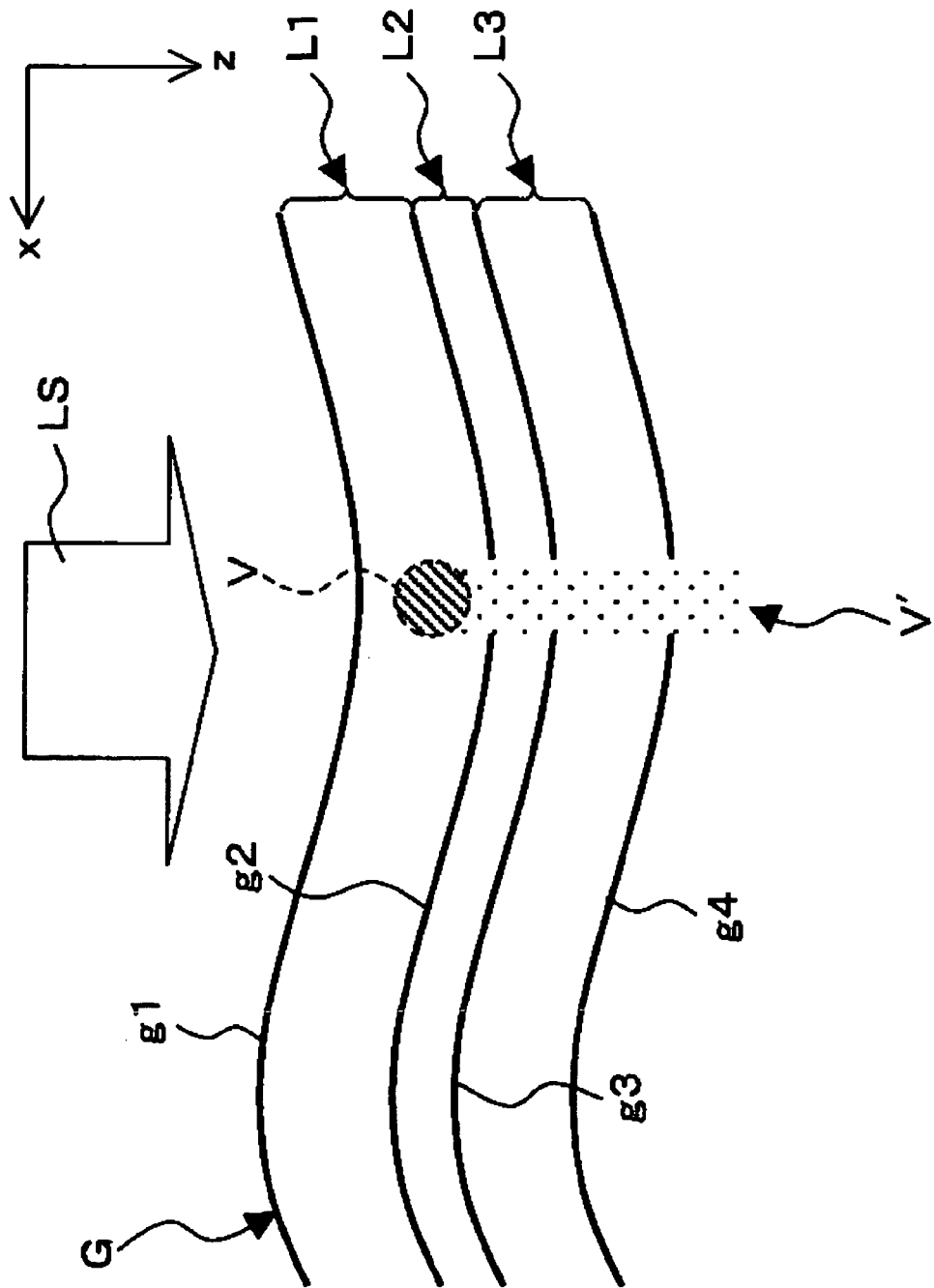
FIG. 7 is a schematic view showing an example of a pattern of a tomographic image formed in the embodiment of the fundus oculi observation device according to the present invention.

Symbol V in FIG. 7 denotes an image region corresponding to the cross section of the fundus blood vessel (a vascular cross-sectional region). Moreover, symbol V' denotes an image region located just below the vascular cross-sectional region V (a just-below-blood-vessel region). The vascular region is an image region including the vascular cross-sectional region V and the just-below-blood-vessel region V'.

Symbol LS denotes a radiation direction of the signal light when acquiring the tomographic image G.

The vascular cross-sectional region V and the just-below-blood-vessel region V' are not clearly displayed because of noise caused by a vascular wall, blood, blood flow and so on. Therefore, in the vascular cross-sectional region V and the just-below-blood-vessel region V', the layer regions L2 and L3 and the boundary regions g2-g4 are not clearly depicted. Accordingly, it is difficult to calculate the layer thickness with high accuracy in the vascular cross-sectional region V and the just-below-blood-vessel region V'.

Below, examples of a process of specifying the vascular region in a tomographic image will be described.

In a first process example, the vascular region specifying part 234 analyzes a tomographic image of the fundus oculi Ef and specifies the vascular region. This process is executed in the following manner, for example. In this process example, a predetermined layer position in the tomographic image is previously specified by the layer position specifying part 232. This predetermined layer position shall be, for example, the IS/OS position.

The vascular region specifying part 234 firstly extracts a plurality of pixels located in the depth direction (+z direction and/or −z direction) of the fundus oculi Ef from the tomographic image, with respect to a pixel on the IS/OS position in the tomographic image.

Figure 8:
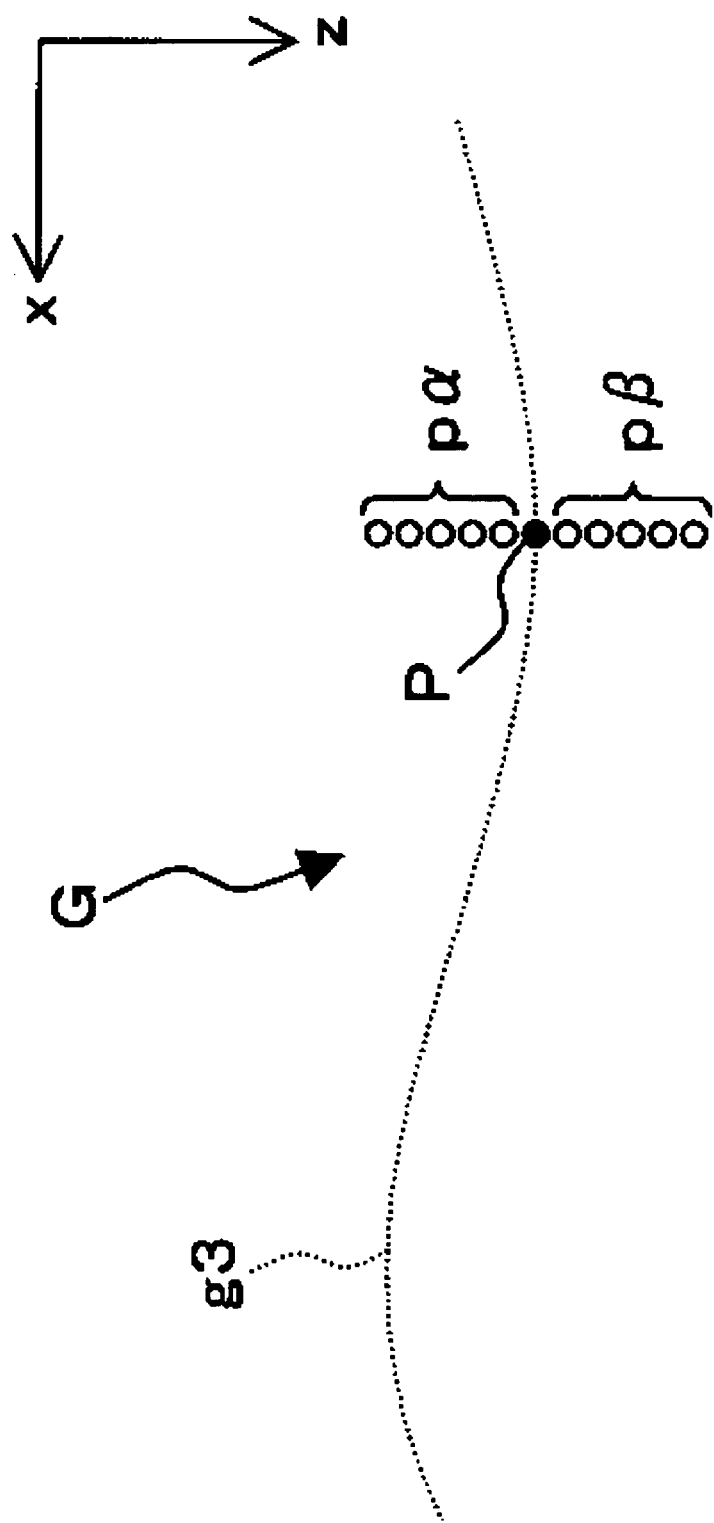
FIG. 8 is a schematic explanation view for explaining an example of a process of specifying a vascular position in the embodiment of the fundus oculi observation device according to the present invention.

A specific example of this process is shown in FIG. 8. The boundary region g3 shall be the IS/OS position. Symbol P denotes an arbitrary pixel on the boundary region g3. The vascular region specifying part 234 extracts, from the tomographic image G, pixels pα (α=1-5) located on the side closer to the fundus oculi surface than the pixel P (−z direction) and pixels pβ (β=1-5) located just below the pixel P (+z direction).

The number of pixels to be extracted is arbitrary. Moreover, the number of pixels to be extracted may be identical or different in the +z direction and the −z direction. Moreover, only the pixels along the +z direction may be extracted, or only the pixels along the −z direction may be extracted. Moreover, in a case that there is no pixel on the boundary region g3, it is possible to regard a pixel in the closest position to the boundary region g3 as a pixel on the boundary region g3.

Next, the vascular region specifying part 234 acquires the respective pixel values (the luminance values) of the pixels pα and pβ (and pixel P), and calculates a statistic that represents variation of these pixel values. As this statistic, it is possible to use an arbitrary value that defines variation of a plurality of pixel values with the plurality of pixel values as the population, such as standard deviation or variance.

Next, the vascular region specifying part 234 determines whether this statistic is included in a predetermined range. For example, in a case that the statistic is standard deviation or variance, it is possible to set a range equal to or less than a certain threshold as the predetermined range. To be specific, in a case that the threshold is denoted by $\Sigma$ and the statistic corresponding to the pixel P is standard deviation $\sigma(P)$, the vascular region specifying part 234 determines whether $\sigma(P) \leq \Sigma$ is satisfied.

The threshold $\Sigma$ is set based on the following characteristic of the tomographic image G, for example. The tomographic image G is an image showing the fine structure (the layer region and the boundary region) of the fundus oculi Ef, but cannot represent the fine structure of the vascular region. In a case that the tomographic image G is a luminance image, the vascular region is represented almost uniformly in black. That is to say, the pixels in the vascular region almost uniformly have low luminance values. The threshold $\Sigma$ is used for determining whether the pixel on the boundary region g3 is a pixel in the vascular region. For example, this threshold $\Sigma$ can be determined by, for a number of tomographic images, comparing the standard deviation of the luminance values of pixels in the vascular region with the standard deviation of the luminance values of pixels of the other image region and statistically processing (for example, averaging) the comparison result. The method for determining the threshold $\Sigma$ is not limited to the above method. Moreover, statistics other than standard deviation can also be determined in the same way.

The vascular region specifying part 234 executes such determination on each pixel P on the boundary region g3. Then, the vascular region specifying part 234 specifies such a pixel that a statistic is included in a predetermined value. In the above specific example, the vascular region specifying part 234 specifies such a pixel P on the boundary region g3 that the standard deviation $\sigma(P)$ is equal to or less than the threshold $\Sigma$. Consequently, the following set S of pixels is obtained: S={the pixel P on the boundary region g3: $\sigma(P) \leq \Sigma$}.

The set S is a set of pixels determined to be located in the vascular region among the pixels P on the boundary region g3. The vascular region specifying part 234 specifies the vascular region in the tomographic image in the above manner. This is the end of the description of the first example of the process.

A second process example by the vascular region specifying part 234 will be described. In a case that the second process example is applied, a plurality of tomographic images at different cross-sectional positions are acquired in advance. The plurality of tomographic images have cross sections parallel to each other, for example (refer to tomographic images G1-Gm shown in FIG. 10).

The vascular region specifying part 234 firstly accumulates the plurality of tomographic images in the depth direction (the z-direction) of the fundus oculi Ef, respectively, to form an accumulated image.

This process is executed in the following manner, for example.

The tomographic image is an image formed by arranging depthwise images (one-dimensional images) at the radiation positions (the scan points) of the signal light LS. The vascular region specifying part 234 accumulates the pixel values of pixels in the respective one-dimensional images, thereby forming an accumulated image.

The accumulated image is an image that artificially expresses the surface morphology of the fundus oculi Ef in a scan region of the signal light LS, and a similar image to the fundus oculi image Ef' captured by the retinal cameral unit 1A. After the description of FIG. 10, an example of the process of forming the accumulated image from the tomographic images G1-Gm will be described.

Next, the vascular region specifying part 234 analyzes the accumulated image and obtains running position information that represents the running position of a blood vessel in the fundus oculi Ef. The accumulated image is an image that artificially expresses the surface morphology of the fundus oculi Ef as described above. The accumulated image includes an image corresponding to the blood vessel of the fundus oculi Ef (a vascular image).

The vascular region specifying part 234 extracts the vascular image in the accumulated image, for example, in the following manner.

Firstly, the vascular region specifying part 234 executes a predetermined filtering process on the accumulated image. In this filtering process, for example, a process for making it easy to distinguish the vascular region in the accumulated image from other image regions is executed, such as a tone conversion process, an image enhancement process, a contrast conversion process, an edge detection process, an image averaging process and an image smoothing process.

Next, the vascular region specifying part 234 binarizes the accumulated image based on a predetermined threshold. This threshold is set in advance based on, for example, the result of analysis of a number of accumulated images. It is also possible to, based on a histogram of the distribution of the pixel values (the luminance values) in an accumulated image, obtain a threshold unique to the accumulated image, and execute the binarizing process based on this threshold. By such a binarizing process, the vascular image in the accumulated image is enhanced.

The vascular region specifying part 234 extracts the vascular image based on the pixel values (the luminance values) of the accumulated image after the binarizing process. Then, the vascular region specifying part 234 specifies the position of the vascular image in the accumulated image, and regards the position information of this vascular image as the running position information. Considering a tomographic image is defined by the xyz coordinate system (or the xy coordinate system) and an accumulated image is formed based on tomographic images, the accumulated image is also an image defined by the xyz coordinate system (or the xy coordinate system).

Accordingly, the running position information is the position information of the vascular image in the accumulated image defined by the coordinate values of the xyz coordinate system (or the xy coordinate system).

Finally, the vascular region specifying part 234 specifies the vascular region in the tomographic image based on the running position information. Here, it is possible to specify the vascular region in the tomographic image along an arbitrary cross-sectional position of the fundus oculi Ef.

For example, since the coordinate system defining the tomographic image used for the process of forming the accumulated image is the same as the coordinate system defining the accumulated image, an image region in the tomographic image having the same coordinate values as the vascular image in the accumulated image is specified, and this image region is set as the vascular region.

Further, in a tomographic image that the cross section is set at an arbitrary position in a definition region of the accumulated image, it is possible to specify a vascular region in the following manner, for example. The tomographic image is formed based on image data of a three-dimensional image (described before). Since the coordinate system defining the accumulated image and the coordinate system defining the image data of the three-dimensional image are the same, an image region in the tomographic image having the same coordinate values as the vascular region in the accumulated image is specified, and this image region is set as the vascular image.

Also in a tomographic image acquired by scanning the definition region of the accumulated image with the signal light LS not based on the image data of the three-dimensional image, it is possible to specify the vascular region in a similar way by referring to scan position information descried later. This is the end of the description of the second example of the process.

A third process example by the vascular region specifying part 234 will be described. In a case that the third example of the process is applied, a plurality of tomographic images as in the second example of the process and the fundus oculi image Ef' are acquired in advance.

The vascular region specifying part 234 firstly analyzes the fundus oculi image Ef' and obtains running position information that represents the running position of a blood vessel in the fundus oculi Ef. This running position information is generated by, for example, executing a filtering process as in the second example of the process on the fundus oculi image Ef', detecting a change in pixel value (luminance value) in the x-direction and the y-direction, specifying a vascular image in the fundus oculi image Ef', and collecting coordinate values of pixels of this vascular image.

Next, the vascular region specifying part 234 forms an accumulated image as in the second example of the process. The accumulated image is, as mentioned before, an image that artificially expresses the surface morphology of the fundus oculi Ef, and an image identical to the fundus oculi image Ef'.

Next, the vascular region specifying part 234 executes position matching of the fundus oculi image Ef' and the accumulated image.

This process can be executed by, for example, executing position matching of a characteristic region in the fundus oculi Ef' (a character region) and a characteristic region in the accumulated image.

The character region is, for example, a vascular region, an image region corresponding to the optic papilla, an image region corresponding to the macula, a branch position of blood vessels, and so on. The position matching of images can be executed by, for example, using known image processing such as pattern matching or image correlation. Through such a position matching process, a coordinate transformation equation between the coordinate system defining the fundus oculi image Ef' and the coordinate system defining the accumulated image is obtained.

Next, the vascular region specifying part 234 specifies an image region in the accumulated image corresponding to a vascular image in the fundus oculi image Ef', based on the result of the above position matching. For example, this process is executed by using the coordinate transformation equation to transform the coordinate values of the vascular image in the fundus oculi image Ef' shown in the running position information into coordinate values of the coordinate system defining the accumulated image. Consequently, the image region (the vascular image) in the accumulated image corresponding to the vascular region in the fundus oculi image Ef' is specified.

Next, the vascular region specifying part 234 specifies a crossing region (a common region) of the vascular image in the accumulated image and the cross section of the tomographic image.

This process can be executed in the same manner as in the second example of the process. This crossing region is defined in an image region corresponding to the fundus oculi surface.

Finally, the vascular region specifying part 234 specifies the vascular region in the tomographic image so as to include this crossing region. The crossing region is defined in the image region corresponding to the fundus oculi surface as described above. The vascular region specifying part 234 sets an image region just below the crossing region in the tomographic image to the vascular region. For example, in a case that the coordinate values of the crossing region are (x,y), the vascular region specifying part 234 sets an image region defined by coordinate values (x,y,z) to the vascular region as the vascular region.

Thus, in the third example of the process, a vascular region in the fundus oculi image Ef' is specified, an image region in an accumulated image corresponding to this vascular region is specified, and a common region of this image region and the tomographic image is set to a vascular region in the tomographic image. In general, the fundus oculi image Ef' is a clearer image than an accumulated image.

Therefore, a vascular region extracted from the fundus oculi image Ef' has higher accuracy and precision than a vascular region extracted from an accumulated image (the second process example).

Accordingly, in the third example of the process, it is possible to set a vascular region with higher accuracy and precision than in the second example of the process. Since the accuracy and precision in the third example of the process depends on the position matching process between the fundus oculi image Ef' and the accumulated image, it is necessary to favorably execute this position matching process.

The image processor 230 described above includes the microprocessor 201, the RAM 202, the ROM 203, the hard disk drive 204 (the control program 204a) and so on.

(User Interface)

The user interface (UI) 240 is provided with a display 240A and a manipulation part 240B. The display 240A is composed of a display device such as the display 207. Moreover, the manipulation part 240B is composed of an input device and a manipulation device such as the keyboard 205 and the mouse 206

[Scan with Signal Light and Image Processing]

An example of the scan pattern of the signal light LS and the image processing pattern will be described. A scan with the signal light LS is executed by the scan unit 141. To be specific, the scan with the signal light LS is executed by control of the mirror drive mechanisms 241 and 242 by the controller 210 to change the directions of the reflecting surfaces of the Galvano mirrors 141A and 141B.

The Galvano mirror 141A scans with the signal light LS in the horizontal direction (the x-direction in FIG. 1). The Galvano mirror 141B scans with the signal light LS in the vertical direction (the y-direction in FIG. 1). Moreover, by operating both the Galvano mirrors 141A and 141B simultaneously, it is possible to scan with the signal light LS in any direction on the xy plane.

Figure 9A:
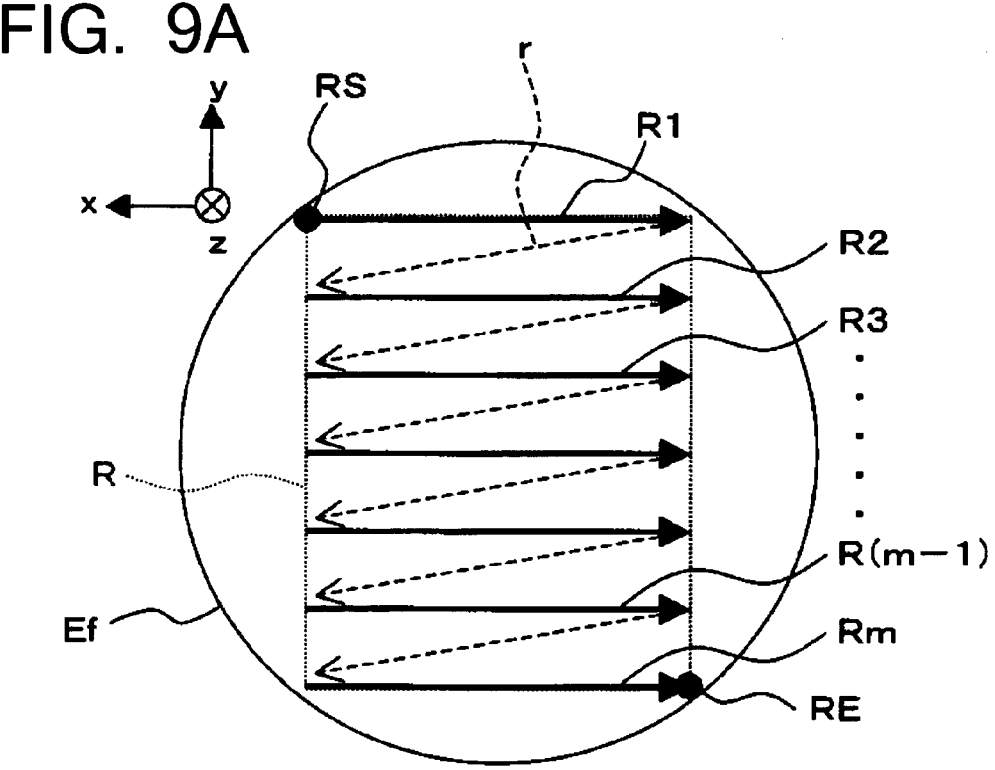
FIGS. 9A and 9B are schematic views showing an example of a scan pattern of a signal light in the embodiment of the fundus oculi observation device according to the present invention.
Figure 9B:
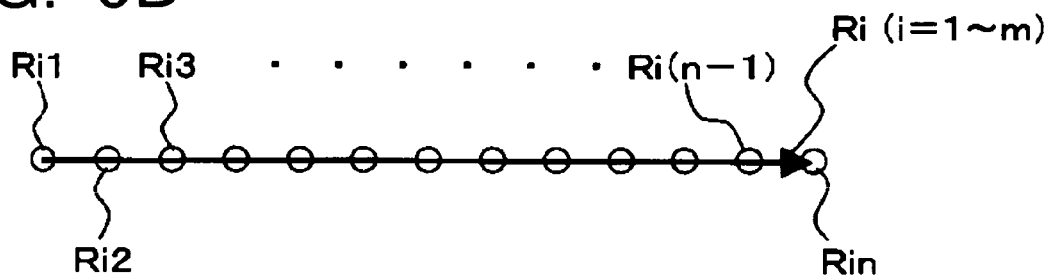

FIGS. 9A and 9B show an example of the scan pattern of the signal light LS for forming an image of the fundus oculi Ef. FIG. 9A shows an example of the scan pattern of the signal light LS, when the fundus oculi Ef is seen from a direction that the signal light LS enters the eye E (that is, seen from −z side toward +z side in FIG. 1).

Moreover, FIG. 9B shows an example of an arrangement pattern of the scan points (measurement positions) on each scan line on the fundus oculi Ef.

As shown in FIG. 9A, a scan with the signal light LS is executed within a rectangular scan region R. Within this scan region R, a plurality of (m lines of) scan lines R1-Rm along the x-direction are set.

Scan lines Ri (i=1-m) are arranged in the y-direction. A direction of each of the scan lines Ri (the x-direction) will be referred to as the "main scan direction" and a direction orthogonal thereto (the y-direction) will be referred to as the "sub-scan direction."

On each of the scan lines Ri, as shown in FIG. 9B, a plurality of (n pieces of) scan points Ri1-Rin are set. The positions of the scan region R, the scan lines Ri and the scan points Rij are properly set before execution of a measurement.

In order to execute the scan shown in FIGS. 9A and 9B, the controller 210 firstly controls the Galvano mirrors 141A and 141B to set the incident target of the signal light LS into the fundus oculi Ef to a scan start position RS (a scan point R11) on the first scan line R1.

Subsequently, the controller 210 controls the low-coherence light source 160 to flash the low-coherence light L0, thereby making the signal light LS enter the scan start position RS. The CCD 184 receives the interference light LC based on the reflected light of this signal light LS at the scan start position RS, accumulates electric charges, and generates a detection signal.

Next, the controller 210 controls the Galvano mirror 141A to scan with the signal light LS in the main scan direction to set the incident target to a scan point R12, and flashes the low-coherence light L0 to make the signal light LS enter the scan point R12. The CCD 184 receives the interference light LC based on the reflected light of this signal light LS at the scan point R12, accumulates electric charges, and generates a detection signal.

Likewise, the controller 210 controls to generate a detection signal corresponding to each of the scan points, by flashing the low-coherence light L0 at each of the scan points while sequentially moving the incident target of the signal light LS from a scan point R13 to R14, - - - , R1(n−1), and R1n.

When the measurement at a last scan point R1n on the first scan line R1 is finished, the controller 210 simultaneously controls the Galvano mirrors 141A and 141B to move the incident target of the signal light LS to a first scan point R21 on a second scan line R2 following a line switching scan r. Then, the controller 210 controls to execute the same measurement on each of scan points R2j (j=1-n) on this second scan line R2 and to generate a detection signal corresponding to each of the scan points R2j.

Likewise, the controller 210 controls to execute a measurement on each of a third scan line R3, - - - , an m−1th scan line R(m−1), an mth scan line Rm and to generate a detection signal corresponding to each scan point. Symbol RE on the scan line Rm denotes a scan end position corresponding to a scan point Rmn.

Thus, the controller 210 controls to generate m×n pieces of detection signals corresponding to m×n pieces of scan points Rij (i=1-m, j=1-n) within the scan region R. A detection signal corresponding to each of the scan points Rij may be denoted by Dij.

In the above control, when the Galvano mirrors 141A and 141B are operated, the controller 210 acquires position information (coordinates in the xy coordinate system) of each of the scan points Rij. This position information (scan position information) is referred to when an OCT image is formed, for example.

Next, an example of image processing when the scan shown in FIGS. 9A and 9B is executed will be described.

The image forming part 220 forms tomographic images of the fundus oculi Ef along the respective lines Ri (the main scan direction).

Moreover, the image processor 230 forms a three-dimensional image of the fundus oculi Ef based on the tomographic images formed by the image forming part 220.

The tomographic image forming process includes a two-step arithmetic process as conventional. In the first step, based on each detection signal Dij, an image in the depth direction (the z-direction in FIG. 1) of the fundus oculi Ef at the scan point Rij is formed.

In the second step, the depthwise images at the scan points Ri1-Rin are arranged based on the scan position information, and a tomographic image Gi along the scan line Ri is formed. Through the above process, m pieces of tomographic images G1-Gm are obtained.

The image processor 230 arranges the tomographic images G1-Gm based on the scan position information and executes an interpolating process of interpolating an image between the adjacent tomographic images Gi and G(i+1), thereby generating a three-dimensional image of the fundus oculi Ef. This three-dimensional image is defined by the three-dimensional coordinates (x,y,z) based on the scan position information, for example.

Further, the image processor 230 is capable of forming a tomographic image at an arbitrary cross-section, based on this three-dimensional image. When the cross-section is designated, the image processor 230 specifies the position of each scan point (and/or an interpolated depthwise image) on the designated cross-section, extracts a depthwise image (and/or an interpolated depthwise image) at each specified position from the three-dimensional image, and arranges a plurality of extracted depthwise images based on the scan position information and so on, thereby forming a tomographic image at the designated cross-section.

An image Gmj shown in FIG. 10 represents a depthwise image at the scan point Rmj on the scan line Rm. Likewise, a depthwise image at the scan point Rij formed in the aforementioned first-step is represented as an "image Gij."

Here, an example of a process of forming an accumulated image based on the tomographic images G1-Gm will be described. The vascular region specifying part 234 accumulates the image Gij composing the tomographic image Gi in the depth direction (the z-direction) to form a dotted image.

"Accumulating in the depth direction" means a calculation of summing (projecting) the luminance values of pixels composing the image Gij in the depth direction. Therefore, the dotted image obtained by accumulating the image Gij has such a luminance value that the luminance values at the respective z-positions of the image Gij are summed in the depth direction. Moreover, the position of the dotted image has the same coordinate values as that of the image Gij in the xy-coordinate system.

The vascular region specifying part 234 executes the abovementioned accumulation process on each of the m pieces of tomographic images G1-Gm obtained by a series of scans with the signal light LS. Consequently, an accumulated image formed by m×n pieces of dotted images that are two-dimensionally distributed in the scan region R is formed. This accumulated image is an image that represents the morphology of the surface of the fundus oculi Ef, as well as the fundus oculi image Ef' in the scan region R.

The scan pattern of the signal light LS is not limited to the abovementioned one. For example, it is possible to scan with the signal light LS only in the horizontal direction (the x-direction), only in the perpendicular direction (the y-direction), in the longitudinal and lateral directions like a cruciform, radially, circularly, concentrically, or helically. That is to say, as mentioned before, the scan unit 141 is configured to be capable of independently scanning with the signal light LS in the x-direction and the y-direction, so that it is possible to scan with the signal light LS along an arbitrary trajectory on the xy-plane.

[Usage Pattern]

A usage pattern of the fundus oculi observation device 1 will be described. The flow charts shown in FIGS. 11 and 12 respectively show examples of the usage pattern of the fundus oculi observation device 1.

Figure 11:
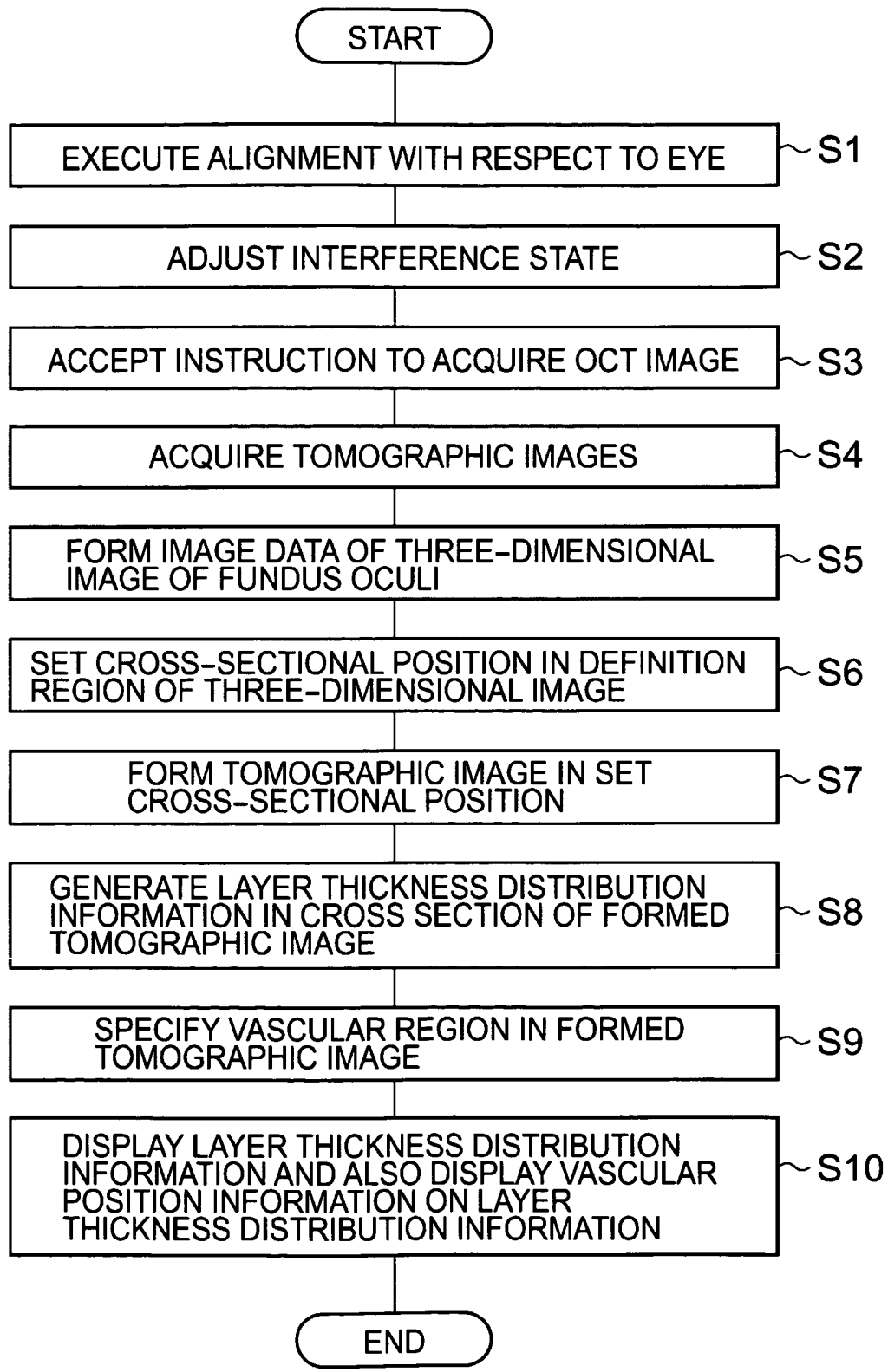
FIG. 11 is a flow chart showing an example of a usage pattern in the embodiment of the fundus oculi observation device according to the present invention.
Figure 12:
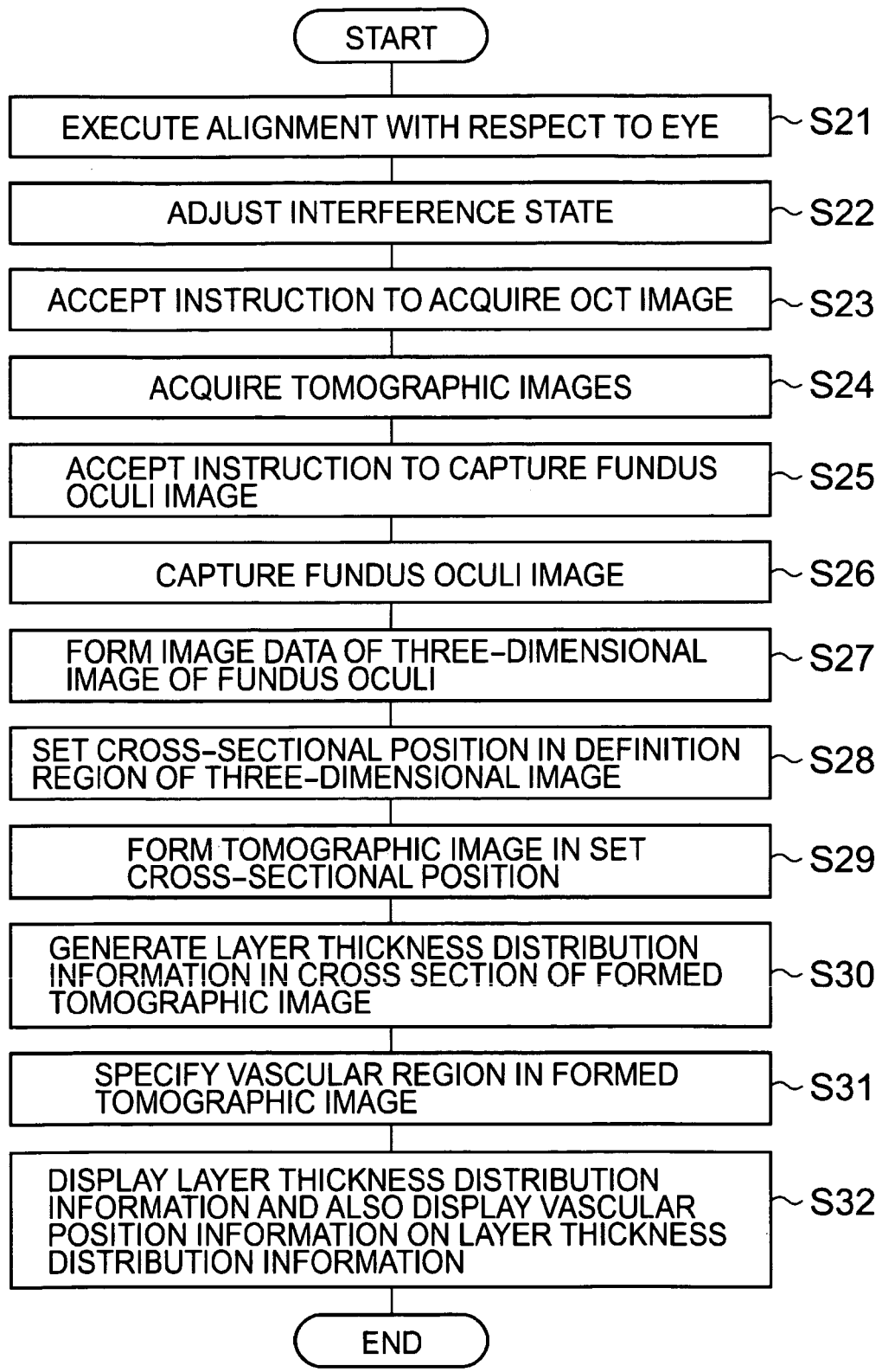
FIG. 12 is a flow chart showing an example of a usage pattern in the embodiment of the fundus oculi observation device according to the present invention.

The usage pattern shown in FIG. 11 is an example of specification of a vascular region based on a tomographic image. The usage pattern shown in FIG. 12 is an example of specification of a vascular region based on a fundus oculi image Ef' and a tomographic image.

[First Usage Pattern]

With reference to FIG. 11, a first usage pattern of the fundus oculi observation device 1 will be described. Although not described in FIG. 11, it is possible to properly capture the fundus oculi image Ef' in this usage pattern.

Firstly, alignment of an optical system with the eye E is executed (S1). The alignment is executed as in a conventional retinal camera. For example, the alignment is executed by adjusting the position of the retinal camera unit 1A while projecting an alignment bright point (not shown) to the eye E to observe the state thereof.

Next, the position of the reference mirror 174 is adjusted, and the interference state of the signal light and the reference light is adjusted (S2). Here, the adjustment is executed so that an image at a desired depth position of the fundus oculi Ef becomes clear. For example, the interference state is adjusted so that the IS/OS position of the fundus oculi Ef can be visually recognized clearly. The position adjustment of the reference mirror 174 may be manually performed by using the manipulation part 240B, or may be automatically performed.

When the adjustment of the interference state is finished, the operator executes a predetermined manipulation by the manipulation part 240B to instruct acquisition of an OCT image (S3).

The main controller 211 having received a signal based on this instruction through the manipulation part 240B controls the low-coherence light source 160, the scan unit 141, the CCD 184, the image forming part 220 and so on to acquire an OCT image (S4). Here, it is assumed that, as the OCT image, the tomographic images G1-Gm shown in FIG. 10 are acquired.

The image processor 230 forms image data of a three-dimensional image of the fundus oculi Ef based on the tomographic images Gi (S5).

Next, a cross-sectional position is set within a definition region (the scan region R) of this three-dimensional image (S6). The setting of the cross-sectional position may be manually executed by the operator, or may be automatically executed by the fundus oculi observation device 1.

In the former case, for example, the three-dimensional image is displayed on the display 240A, and the cross-sectional position is set by using the manipulation part 240B with reference to the displayed image. Moreover, in a case that the fundus oculi image Ef' is captured in advance, the cross-sectional position may be set while the fundus oculi image Ef' is displayed. In this case, position matching of the fundus oculi image Ef' and the three-dimensional image is executed by using the accumulated image, for example.

In the latter case, for example, the image processor 230 automatically sets a predetermined cross-sectional position. Here, the image processor 230 analyzes the three-dimensional image and specifies a region in the three-dimensional image corresponding to the cross-sectional position. As a specific example, the image processor 230 analyzes the three-dimensional image to search for the deepest part of a depression on the fundus oculi surface as the fovea centralis, and sets a circular region having a predetermined radius about this fovea centralis as the cross-sectional position. Below, a case that such a circular cross-sectional position is set will be described.

The image processor 230 forms a tomographic image at this circular cross-sectional position based on the image data of the three-dimensional image (S7).

The layer thickness distribution calculator 231 generates layer thickness distribution information that represents the distribution of the thicknesses of the layer of the fundus oculi Ef in the cross section of the tomographic image (S8).

The vascular region specifying part 234 specifies the vascular region in this tomographic image (S9). Here, the aforementioned first or second process example will be applied.

The main controller 211 controls the display 240A to display the layer thickness distribution information obtained at step S8 and to also display vascular position information that represents the position of the vascular region obtained at step S9 on the layer thickness distribution information (S10). This is the end of the first usage pattern.

Figure 13:
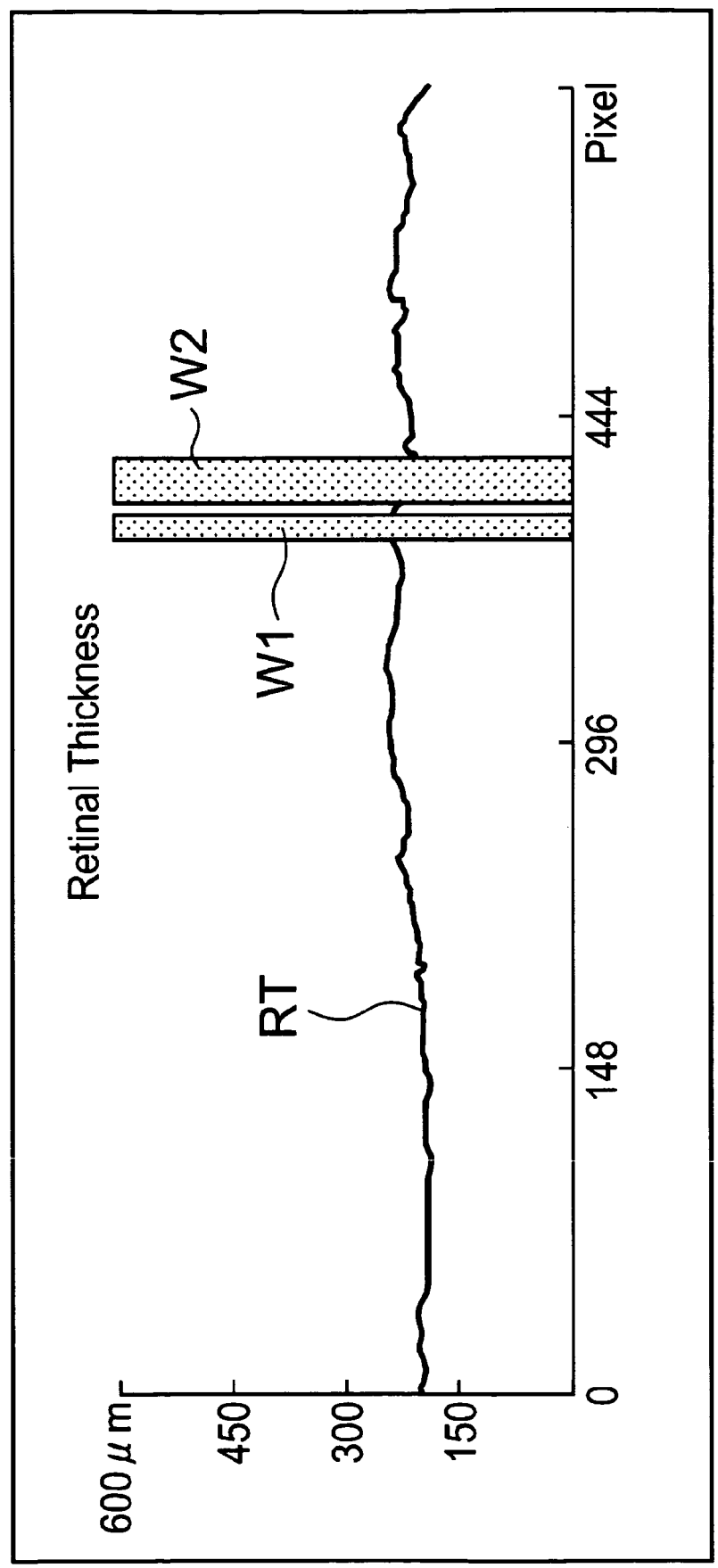
FIG. 13 is a schematic view showing an example of a display pattern of layer thickness distribution information and vascular position information in the embodiment of the fundus oculi observation device according to the present invention.

FIG. 13 shows an example of a display pattern of the layer thickness distribution information and the vascular position information. In this display pattern, a layer thickness graph RT is displayed as the layer thickness distribution information. The horizontal axis of the layer thickness graph RT is defined along the abovementioned circular cross-sectional position. A distance in the horizontal axis direction is defined by the number of pixels. Moreover, the vertical axis of the layer thickness graph RT represents the value of the layer thickness. The unit of the value of the layer thickness is μm.

Thus, the layer thickness graph RT represents the distribution of the layer thicknesses at the cross-sectional position.

In this example, it is assumed that, at step S9, two vascular regions (first and second vascular regions) are specified in the tomographic image. In this display pattern, as shown in FIG.

13, vascular position information W1 representing the position of the first vascular region and vascular position information W2 representing the position of the second vascular region are included. The respective vascular position information W1 and W2 are images (vascular position images) extending in the vertical axis direction displayed at positions of the vascular regions in the cross section.

Thus, by displaying the vascular position information W1 and W2 on the layer thickness graph RT, it is possible to easily grasp which position on the layer thickness graph RT corresponds to the vascular region. In other words, by the vascular position information W1 and W2, it is possible to easily grasp at which position of the cross section of the tomographic image the layer thickness has not been analyzed with accuracy.

Although the layer thickness graph RT is interrupted at the display positions of the vascular position information W1 and W2 in FIG. 13, a continuous layer thickness graph RT may be displayed by using the result of the analysis at the display position.

Figure 14:
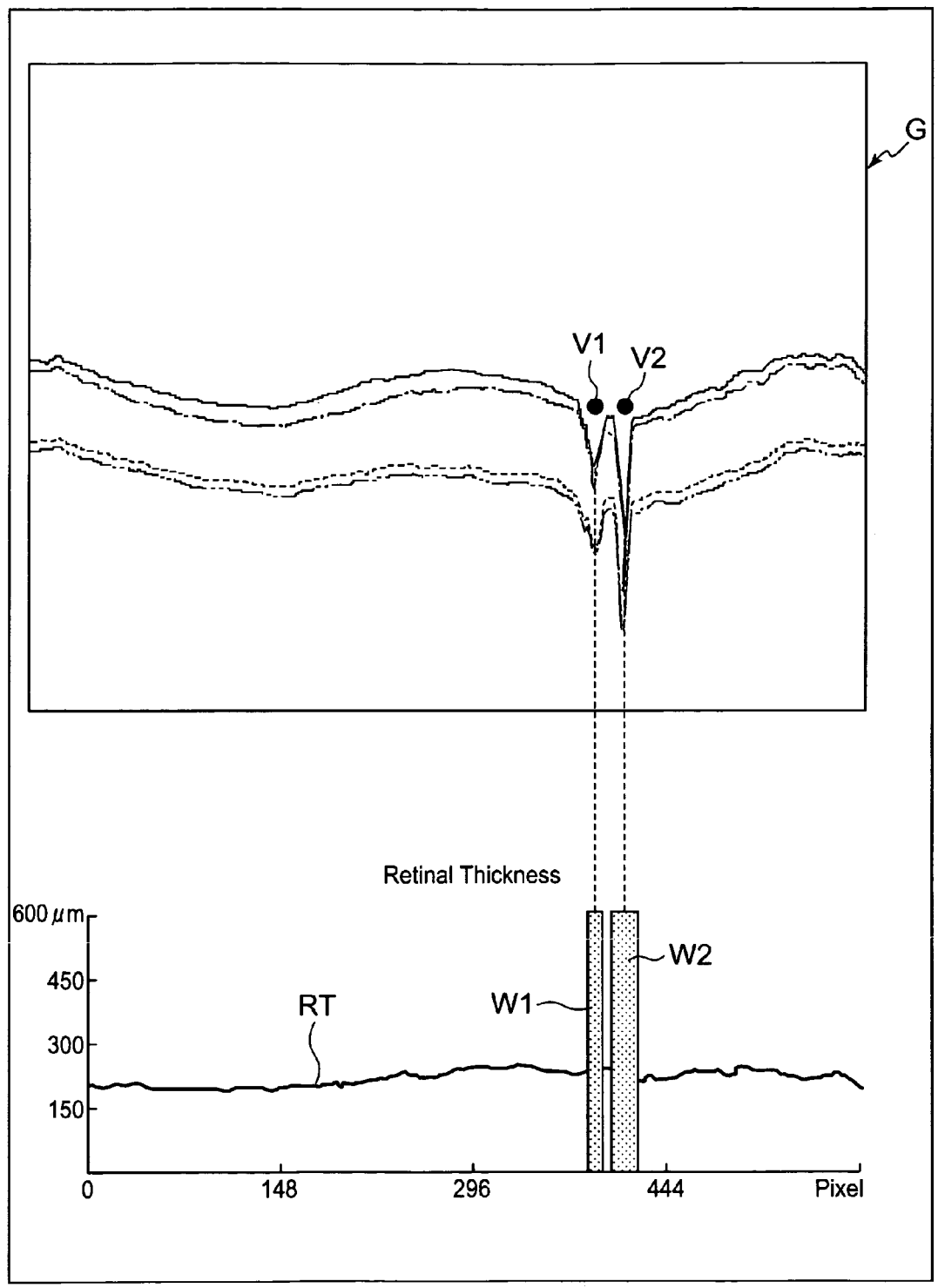
FIG. 14 is a schematic view showing an example of a display pattern of layer thickness distribution information and vascular position information in the embodiment of the fundus oculi observation device according to the present invention.

Another display pattern is shown in FIG. 14. In the display pattern of FIG. 14, together with the layer thickness distribution information and the vascular position information, the tomographic image formed at step S7 is displayed.

In this display pattern, the tomographic image G of the fundus oculi Ef and the layer thickness graph RT are displayed side by side.

The tomographic image G has been formed at step S7. The display size of the tomographic image G is adjusted to the display size of the layer thickness graph RT. On the layer thickness graph RT, the vascular position information W1 and W2 are displayed as in FIG. 13.

The parallel display of the tomographic image G and the layer thickness graph RT will be described in more detail. The tomographic image G and the layer thickness graph RT are displayed longitudinally side by side. The tomographic image G is displayed so that a direction (the horizontal direction) along the cross section coincides with the horizontal axis direction of the layer thickness graph RT. Moreover, the size in the horizontal direction of the tomographic image G coincides with the horizontal size of the layer thickness graph RT.

On the tomographic image G, images V1 and V2 representing the vascular cross-sectional region (vascular cross-sectional images) are displayed. The vascular cross-sectional region has been described before (refer to FIG. 7). In the tomographic image G, the first vascular region includes the vascular cross-sectional image V1 and a region just below the image V1. In the same way, the second vascular region includes the vascular cross-section image V2 and a region just below the image V2.

The vascular position information W1 represents a position corresponding to the first vascular region on the layer thickness graph RT. Likewise, the vascular position information W2 represents a position corresponding to the second vascular region on the layer thickness graph RT.

The vascular cross-sectional image V1 and the vascular position information W1 are displayed at the same positions in the horizontal direction (the horizontal axis direction). Consequently, the display position of the first vascular region in the tomographic image G and the display position of the vascular position information W1 in the layer thickness graph RT are associated with each other.

In the same way, the vascular cross-sectional image V2 and the vascular position information W2 are displayed at the same position in the horizontal direction (the horizontal axis direction). Consequently, the display position of the second vascular region in the tomographic image G and the display position of the vascular position information W2 in the layer thickness graph RT are associated with each other.

Thus displaying the layer thickness graph RT and the tomographic image G side by side has an advantage that it is possible to grasp both the state of the cross section of the fundus oculi Ef and the layer thickness.

Further, displaying the vascular position information W1 and W2 on the layer thickness graph RT and the vascular regions (the vascular cross-sectional images V1 and V2) in the tomographic image G by associating the displayed positions with each other has an advantage that it is possible to grasp the relation between the vascular position in the tomographic image and the layer thickness graph RT.

[Second Usage Pattern]

With reference to FIG. 12, a second usage pattern of the fundus oculi observation device 1 will be described. Firstly, alignment of the optical system with the eye E is executed (S21), and further, the interference state of the signal light and the reference light is adjusted (S22).

When the operator instructs acquisition of an OCT image (S23), the fundus oculi observation device 1 acquires an OCT image (S24).

Here, it is assumed that the tomographic images G1-Gm are acquired as the OCT image.

Next, the operator instructs to capture a two-dimensional image of the surface of the fundus oculi Ef (S25). The main controller 211 controls the retinal camera unit 1A to capture the fundus oculi image Ef' (S26). The timing of capturing the fundus oculi image Ef' may be before the acquisition of the OCT image.

The image processor 230 forms image data of a three-dimensional image of the fundus oculi Ef based on the tomographic images Gi acquired at step S24 (S27).

Next, a cross-sectional position is set within a definition region (the scan region R) of the three-dimensional image (S28). The setting of the cross-sectional position may be manually executed by the operator, or may be automatically executed by the fundus oculi observation device 1 as in the first usage pattern.

The image processor 230 forms a tomographic image at this circular cross-sectional position based on the image data of the three-dimensional image (S29).

The layer thickness distribution calculator 231 generates layer thickness distribution information that represents the distribution of the thickness of the layer of the fundus oculi Ef at the cross section of this tomographic image (S30).

The vascular region specifying part 234 specifies a vascular region in this tomographic image (S31). This process is executed by applying the aforementioned third process example based on the fundus oculi image Ef' captured at step S26 and on the image data of the three-dimensional image formed at step S27.

The main controller 211 controls the display 240A to display the layer thickness distribution information obtained at step S30 and to also display vascular position information representing the position of the vascular region obtained at step S31 on the layer thickness distribution information (S32). This is the end of the second usage pattern.

A display pattern of the layer thickness distribution information and the vascular position information will be described. In the case of displaying only the layer thickness distribution information and the vascular position information, it is possible to apply the same display pattern as in FIG. 13. Moreover, in the case of displaying the tomographic image together with the layer thickness distribution information and the vascular position information, it is possible to apply the same display pattern as in FIG. 14.

Figure 15:
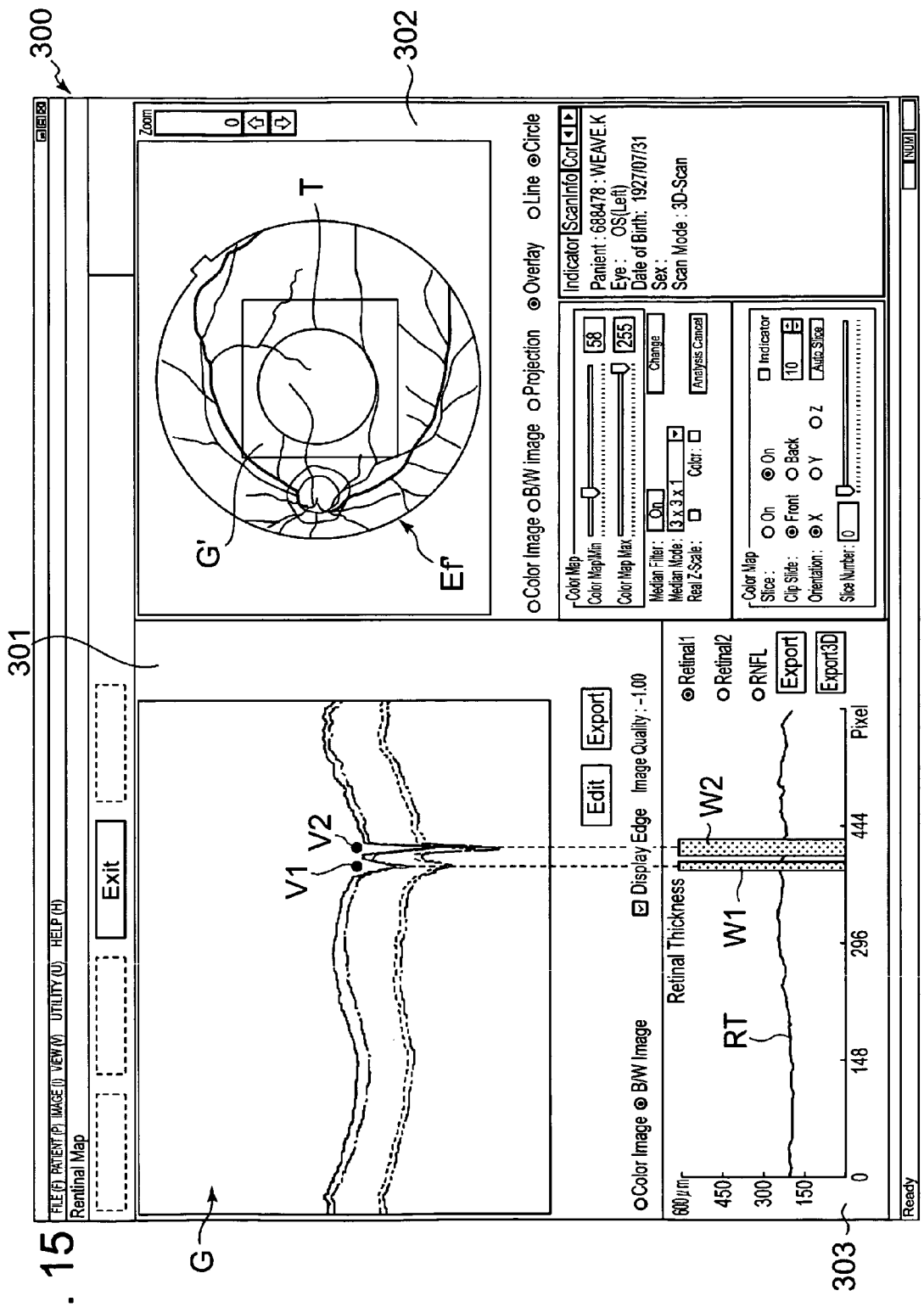
FIG. 15 is a schematic view showing an example of a display pattern of layer thickness distribution information and vascular position information in the embodiment of the fundus oculi observation device according to the present invention.

In the second usage pattern, the fundus oculi image Ef' is captured at step S26. FIG. 15 describes a display screen 300 for displaying the fundus oculi image Ef' together with the layer thickness information, the vascular position information and the tomographic image.

The display screen 300 is provided with a tomographic image display 301, a fundus oculi image display 302, and a layer thickness distribution information display 303. The tomographic image display 301 and the fundus oculi image display 302 are arranged side by side laterally on the screen. Moreover, the tomographic image display 301 and the layer thickness distribution information display 303 are arranged side by side longitudinally on the screen.

On the tomographic image display 301, the tomographic image G at the circular cross-sectional position formed at step S29 is displayed.

On the fundus oculi image display 302, the fundus oculi image Ef' captured at step S26 is displayed. On the layer thickness distribution information display 303, the layer thickness graph RT generated at step S30 is displayed.

As in FIGS. 13 and 14, the vascular cross-sectional images V1 and V2 are displayed on the tomographic image G. The vascular cross-sectional image V1 and the vascular position information W1 are displayed at the same position in the horizontal direction (the horizontal axis direction). Consequently, the display position of the first vascular region in the tomographic image G and the display position of the vascular position information W1 in the layer thickness graph RT are associated with each other. Moreover, on the layer thickness graph RT, the vascular position information W1 and W2 are displayed. The vascular cross-section image V2 and the vascular position information W2 are displayed at the same position in the horizontal direction (the horizontal axis direction). Consequently, the display position of the second vascular region in the tomographic image G and the display position of the vascular position information W2 in the layer thickness graph RT are associated with each other.

On the fundus oculi image Ef', an accumulated image G' is displayed. The accumulated image G' is displayed at a position on the fundus oculi image Ef' based on the result of the position matching process described before. Moreover, a cross-sectional position image T is displayed on the fundus oculi image Ef'. The cross-sectional position image T represents the circular cross-sectional position of the tomographic image G.

Thus displaying the layer thickness distribution information, the vascular position information, the tomographic image and the fundus oculi image Ef' has an advantage that it is possible to grasp the information together.

Further, by displaying the cross-sectional position image T on the fundus oculi image Ef', it is possible to easily grasp the cross-sectional position of the tomographic image G on the fundus oculi image Ef'. Moreover, by the cross-sectional position image T, it is possible to easily grasp in which region on the fundus oculi Ef' the layer thickness has been measured.

[Actions and Effects]

The actions and effects of the fundus oculi observation device 1 will be described.

The fundus oculi observation device 1 forms the plurality of tomographic images G1-Gm of the fundus oculi Ef and, for the tomographic image G based on the tomographic images G1-Gm, calculates the layer thickness distribution of the fundus oculi Ef in the cross section. Moreover, the fundus oculi observation device 1 specifies a vascular region in the tomographic image G. Furthermore, the fundus oculi observation device 1 displays the layer thickness distribution information that represents the calculated layer thickness distribution, and also displays the vascular position information representing the position of the specified vascular region on the layer thickness distribution information.

According to the fundus oculi observation device 1, it is possible to define which part of the analysis result (the layer thickness distribution information) of the layer thickness of the fundus oculi Ef is a part having been obtained by analyzing the vascular region. Thus, by reflecting the position of the blood vessel to the analysis result of the layer thickness, it is possible to increase the precision of diagnosis referring to the layer thickness.

Further, the fundus oculi observation device 1 forms the plurality of tomographic images G1-Gm of the fundus oculi Ef, and captures a two-dimensional image (the fundus oculi image Ef') of the surface of the fundus oculi Ef. The fundus oculi observation device 1, for the tomographic image G based on the tomographic images G1-Gm, calculates the layer thickness distribution of the fundus oculi Ef in the cross section. Moreover, the fundus oculi observation device 1 obtains the running position information that represents the running position of the blood vessel in the fundus oculi Ef based on the fundus oculi image Ef', and specifies the vascular region in the tomographic image G based on this running position information. Furthermore, the fundus oculi observation device 1 displays the layer thickness distribution information representing the calculated layer thickness distribution information, and also displays the vascular position information representing the position of the specified vascular region on the layer thickness distribution information.

According to the fundus oculi observation device 1, it is possible to define which part of the analysis result (the layer thickness distribution information) of the layer thickness of the fundus oculi Ef is a part having been obtained by analyzing the vascular region. Thus, by reflecting the position of the blood vessel to the analysis result of the layer thickness, it is possible to increase the precision of diagnosis referring to the layer thickness.

Further, the fundus oculi observation device 1 forms the tomographic image G at a new cross section based on the plurality of tomographic images G1-Gm of the fundus oculi Ef, and obtains the layer thickness distribution information of the fundus oculi Ef in this new cross section. Further, the fundus oculi observation device 1 specifies the vascular region in the new tomographic image G.

Furthermore, the fundus oculi observation device 1 displays the vascular position information representing the position of the new vascular region on the layer thickness distribution information representing the new layer thickness distribution.

With such a configuration, it is possible to acquire and display the layer thickness distribution information and the vascular region in an arbitrary cross-sectional position in a measurement range (the scan region R) of the tomographic images G1-Gm.

Modification

The configuration described above is merely an example for favorably implementing the fundus oculi observation device relating to the present invention. Therefore, it is possible to properly apply any modification within the scope of the present invention.

For example, the layer thickness distribution information is not limited to the layer thickness graph of the above embodiment, and may be arbitrary information that represents the distribution of the thicknesses of the layer of the fundus oculi at a certain cross-sectional position.

Further, the vascular position information is not limited to the vascular position information of the above embodiment, and may be arbitrary information that represents a part in the layer thickness distribution information corresponding to a vascular region in a tomographic image. For example, it is possible to configure to change the display color of a part of the layer thickness graph corresponding to the vascular region.

Further, the process of generating the layer thickness distribution information of the fundus oculi Ef is not limited to that of the above embodiment. Similarly, the process of specifying a vascular region in a tomographic image is not limited to the three examples of the process of the above embodiment.

Further, in the case of applying a configuration in which a fundus oculi image is not captured, it is not necessary to install a configuration for capturing a fundus oculi image, and it is sufficient to install only a configuration for acquiring an OCT image.

In the above embodiment, the position of the reference mirror 174 is changed and the difference in optical path length between the optical path of the signal light LS and the optical path of the reference light LR is changed. However, the method for changing the difference in optical path length is not limited thereto. For example, by integrally moving the retinal camera unit 1A and the OCT unit 150 with respect to the eye E to change the optical path length of the signal light LS, it is possible to change the difference in optical path length. Moreover, it is also possible to change the difference in optical path length by moving the head of the subject in the depth direction (the z-direction).

[Ophthalmologic Image Processing Device]

An opthalmologic image processing device according to the present invention will be described. The opthalmologic image processing device includes a computer. The opthalmologic image processing device has almost the same configuration as the arithmetic and control unit 200 of the above embodiment. Below, the configuration of the opthalmologic image processing device will be described.

A first configuration example of the opthalmologic image processing device according to the present invention will be described.

This opthalmologic image processing device is provided with an accepting part, a calculator, a specifying part, a display, and a controller.

The accepting part accepts a tomographic image of the fundus oculi from an external device. The accepting part includes, for example, a network adaptor such as a LAN card, and has a function of communicating with an external device via a communication line such as a LAN. The external device is, for example, a storage device such as a NAS, an optical image measurement device that acquires an OCT image, and so on.

Based on the tomographic image accepted by the accepting part (or a tomographic image formed based on this tomographic image), the calculator calculates the layer thickness distribution of the fundus oculi in the cross section of the tomographic image. The calculator has the same configuration as the layer thickness distribution calculator 231 of the above embodiment.

Based on the tomographic image accepted by the accepting part (or a tomographic image formed based on this tomographic image), the specifying part specifies the vascular region in the tomographic image.

The specifying part has the same configuration as the vascular region specifying part 234 of the above embodiment.

The controller controls the display to display the layer thickness distribution information that represents the layer thickness distribution acquired by the calculator. Furthermore, the controller controls to display, on the layer thickness distribution information, the vascular position information that presents the position of the vascular region specified by the specifying part. The controller has the same configuration as the controller 210 of the above embodiment.

According to such an opthalmologic image processing device, it is possible to define which part in the analysis result (the layer thickness distribution information) of the layer thickness of the fundus oculi is the part having been obtained by analyzing the vascular region.

A second configuration example of the opthalmologic image processing device according to the present invention will be described.

This opthalmologic image processing device is provided with an accepting part, a calculator, a specifying part, a display, and a controller, as in the first configuration example.

The accepting part accepts a tomographic image of the fundus oculi and a two-dimensional image of the surface of the fundus oculi.

The specifying part obtains the running position information that represents the running position of a blood vessel in the fundus oculi based on the two-dimensional image, and specifies the vascular region in the tomographic image based on this running position information.

The controller controls the display to display the layer thickness distribution information that represents the layer thickness distribution acquired by the calculator and to also display, on the layer thickness distribution information, the vascular position information that represents the position of the vascular region specified by the specifying part.

According to such an opthalmologic image processing device, it is possible to define which part in the analysis result (the layer thickness distribution information) of the layer thickness of the fundus oculi is the part having been obtained by analyzing the vascular region.

It is possible to properly add an arbitrary configuration described in the above embodiment to the opthalmologic image processing device according to the present invention.

[Program]

A program according to the present invention will be described.

The control program 204a of the above embodiment is an example of the program according to the present invention. The program according to the present invention provides the computer with functions described later.

A first example of the program according to the present invention causes a computer having an accepting part configured to accept a tomographic image of the fundus oculi and a display to function as each of the following parts: (1) a calculator that calculates, based on a tomographic image, the layer thickness distribution of the fundus oculi in the cross section of the tomographic image; (2) a specifying part that specifies, based on a tomographic image, a vascular region in a tomographic image; and (3) a controller that controls the display to display the layer thickness distribution information that represents the layer thickness distribution, and also controls to display, on the layer thickness distribution information, the vascular position information that represents the position of the vascular region.

According to such a program, it is possible to control the computer to specify which part in the analysis result (the layer thickness distribution information) of the layer thickness of the fundus oculi is a part having been obtained by analyzing the vascular region.

A second example of the program according to the present invention causes a computer having an accepting part configured to accept a tomographic image of the fundus oculi and a two-dimensional image of the fundus oculi surface and a display to function as each of the following parts: (1) a calculator that calculates, based on a tomographic image, the layer thickness distribution of the fundus oculi in the cross section of the tomographic image; (2) a specifying part that obtains the running position information representing the running position of a blood vessel in the fundus oculi based on the two-dimensional image and specifies a vascular region in a tomographic image based on this running position information; and (3) a controller that controls the display to display the layer thickness distribution information that represents the layer thickness distribution, and also controls to display, on the layer thickness distribution information, the vascular position information that represents the position of the vascular region.

According to such a program, it is possible to control the computer to specify which part in the analysis result (the layer thickness distribution information) of the layer thickness of the fundus oculi is a part having been obtained by analyzing the vascular region.

The program according to the present invention can be stored into any recording medium that can be read by a computer. As this recording medium, for example, it is possible to use an optical disk, an magneto optical disk (CD-ROM, DVD-RAM, DVD-ROM, MO or the like), a magnetic storage medium (hard disk, Floppy™ disk, ZIP or the like). Moreover, it is also possible to store into a storage device such as a hard disk drive or a memory. Furthermore, it is also possible to transmit this program through a network such as the Internet or LAN.

The invention claimed is:

1. A fundus oculi observation device, comprising:
 a light source configured to output a light;
 an interference-light generator configured to split the light into a signal light and a reference light, and superimpose the signal light propagated through a fundus oculi and the reference light propagated through a reference object to generate an interference light;
 a detector configured to detect the interference light and generate a detection signal;
 an image forming part configured to form a tomographic image of the fundus oculi based on the detection signal;
 a calculator configured to calculate layer thickness distribution of the fundus oculi in a cross section of the tomographic image based on the tomographic image;
 a specifying part configured to specify a vascular region in the tomographic image based on the tomographic image;
 a display; and
 a controller configured to control the display to display a graph having an axis defined along the cross section and an axis taking layer thickness values as layer thickness distribution information representing the layer thickness and to also display a vascular position image representing a position of the vascular region as vascular position information on the layer thickness distribution information.

2. The fundus oculi observation device according to claim 1, further comprising an imaging part configured to capture a two-dimensional image of a surface of the fundus oculi, wherein the specifying part is configured to specify the vascular region based on the tomographic image and the two-dimensional image.

3. The fundus oculi observation device according to claim 2, wherein the specifying part is configured to obtain running position information representing a running position of a blood vessel in the fundus oculi based on the two-dimensional image, and specify the vascular region based on the running position information and the tomographic image.

4. The fundus oculi observation device according to claim 1, wherein the controller is configured to display a tomographic image together with the layer thickness distribution information and the vascular position information.

5. The fundus oculi observation device according to claim 4, wherein the controller is configured to display the vascular position information displayed on the layer thickness distribution information and the vascular region in the tomographic image so that display positions thereof are associated with each other.

6. The fundus oculi observation device according to claim 1, wherein the controller is configured to display a graph having a horizontal axis defined along the cross section and a vertical axis taking layer thickness values, as the layer thickness distribution information, and display a vascular position image representing a position of the vascular region as the vascular position information.

7. The fundus oculi observation device according to claim 6, wherein the controller is configured to display a tomographic image of a display size adjusted to the graph together with the graph, and display the vascular position image at a position on the graph corresponding to the vascular region in the tomographic image.

8. The fundus oculi observation device according to claim 1, wherein:
 the calculator is configured to specify, based on the tomographic image of the fundus oculi, a predetermined layer position in the tomographic image; and
 the specifying part is configured to extract a plurality of pixels located in a depth direction of the fundus oculi with respect to a pixel on the predetermined layer position, calculate a statistic representing variation of pixel values of the plurality of pixels, specify such a pixel on the predetermined layer position that the statistic is included in a predetermined range, and specify the vascular region based on the specified pixel.

9. The fundus oculi observation device according to claim 1, wherein:
 the image forming part is configured to form a plurality of tomographic images at different cross-sectional positions; and
 the specifying part is configured to accumulate the plurality of tomographic images in a depth direction of the fundus oculi to form an accumulated image, obtain running position information representing a running position of a blood vessel in the fundus oculi based on the accumulated image, and specify the vascular region based on the running position information.

10. The fundus oculi observation device according to claim 3, wherein:
 the image forming part is configured to form a plurality of tomographic images at different cross-sectional positions; and
 the specifying part is configured to accumulate the plurality of tomographic images in a depth direction of the fundus oculi to form an accumulated image, execute position matching between the two-dimensional image and the accumulated image, specify, based on a result of the position matching, an image region in the accumulated image corresponding to an image region in the two-dimensional image represented in the running position information, specify a crossing region of the image region in the accumulated image and the cross section of the tomographic image, and set the vascular region so as to include the crossing region.

11. The fundus oculi observation device according to claim 1, wherein:
   the image forming part is configured to form a plurality of tomographic images at different cross-sectional positions, and form a tomographic image at a new cross-sectional position based on the plurality of tomographic images;
   the calculator is configured to calculate layer thickness distribution of the fundus oculi in the new cross section based on the new tomographic image;
   the specifying part is configured to specify a vascular region in the new tomographic image based on the plurality of tomographic images; and
   the controller is configured to control to display vascular position information representing a position of the new vascular region on layer thickness distribution information representing the new layer thickness distribution.

12. The fundus oculi observation device according to claim 11, wherein the controller is configured to display the new tomographic image together with the new layer thickness distribution information and the new vascular region information.

13. An ophthalmologic image processing device, comprising:
   an accepting part configured to accept a tomographic image of a fundus oculi;
   a calculator configured to calculate layer thickness distribution of the fundus oculi in a cross section of the tomographic image based on the tomographic image;
   a specifying part configured to specify a vascular region in the tomographic image based on the tomographic image;
   a display; and
   a controller configured to control the display to display a graph having an axis defined along the cross section and an axius taking layer thickness values as layer thickness distribution information representing the layer thickness distribution, and to also display a vascular position image representing a position of the vascular region as vascular position information on the layer thickness distribution information.

14. A program for causing a computer having an accepting part configured to accept a tomographic image of a fundus oculi and a display to function as:
   a calculator configured to calculate, based on the tomographic image, layer thickness distribution of the fundus oculi in a cross section of the tomographic image;
   a specifying part configured to specify a vascular region in the tomographic image based on the tomographic image; and
   a controller configured to display a graph having an axis defined along the cross section and an axis taking layer thickness values as layer thickness distribution information representing the layer thickness distribution, and also display a vascular position image representing a position of the vascular region as vascular position information on the layer thickness distribution information.

* * * * *